(12) United States Patent
Van Eijk et al.

(10) Patent No.: US 10,316,364 B2
(45) Date of Patent: *Jun. 11, 2019

(54) METHOD FOR IDENTIFYING THE SOURCE OF AN AMPLICON

(71) Applicant: Keygene N.V., Wageningen (NL)

(72) Inventors: Michael Josephus Theresia Van Eijk, Wageningen (NL); Taco Peter Jesse, Wageningen (NL); Adrianus Johannes Van Tunen, Wageningen (NL)

(73) Assignee: KEYGENE N.V., Wageningen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/707,650

(22) Filed: Sep. 18, 2017

(65) Prior Publication Data

US 2018/0002751 A1  Jan. 4, 2018

Related U.S. Application Data

(60) Continuation-in-part of application No. 15/014,642, filed on Feb. 3, 2016, which is a continuation of
(Continued)

(51) Int. Cl.
*C12Q 1/68* (2018.01)
*C12Q 1/6874* (2018.01)
*C12Q 1/6869* (2018.01)

(52) U.S. Cl.
CPC ......... *C12Q 1/6874* (2013.01); *C12Q 1/6869* (2013.01); *C12Q 2535/138* (2013.01)

(58) Field of Classification Search
None
See application file for complete search history.

(56) References Cited

U.S. PATENT DOCUMENTS

| 5,759,822 A | 6/1998 | Chenchik et al. |
| 5,908,978 A | 6/1999 | Amerson et al. |

(Continued)

FOREIGN PATENT DOCUMENTS

| EP | 0 534 858 A1 | 3/1993 |
| EP | 0 976 835 | 2/2000 |

(Continued)

OTHER PUBLICATIONS

Margulies et al. Genome sequencing in microfabricated high-density picolitre reactors. Nature 437:376-380 (2005). (Year: 2005).*

(Continued)

*Primary Examiner* — Samuel C Woolwine
(74) *Attorney, Agent, or Firm* — Foley & Lardner LLP; Sunit Talapatra

(57) ABSTRACT

The present invention relates to a method for identifying the source of an amplicon, comprising: providing a plurality of pools of amplicons from different sources, wherein the amplicons from different sources are present in more than one pool, and wherein the amplicons in each pool are tagged with a unique pool-specific identifier; sequencing at least part of the amplicons that comprise the pool-specific identifiers; and assigning one or more of the amplicons to corresponding pools and/or sources using the pool-specific identifiers.

16 Claims, 8 Drawing Sheets

Specification includes a Sequence Listing.

Related U.S. Application Data application No. 14/613,849, filed on Feb. 4, 2015, now Pat. No. 9,284,606, which is a continuation of application No. 14/219,931, filed on Mar. 19, 2014, now Pat. No. 8,975,028, which is a division of application No. 13/783,601, filed on Mar. 4, 2013, now Pat. No. 8,685,650, which is a continuation of application No. 13/344,162, filed on Jan. 5, 2012, now Pat. No. 8,394,591, which is a division of application No. 12/373,220, filed as application No. PCT/NL2007/000177 on Jul. 10, 2007, now Pat. No. 8,178,300, application No. 15/707,650, which is a continuation of application No. 15/674,126, filed on Aug. 10, 2017, which is a continuation of application No. 15/434,801, filed on Feb. 16, 2017, now Pat. No. 9,745,627, which is a continuation of application No. 15/165,921, filed on May 26, 2016, now Pat. No. 9,574,230, which is a continuation of application No. 13/972,152, filed on Aug. 21, 2013, now Pat. No. 9,376,719, which is a continuation of application No. 13/447,871, filed on Apr. 16, 2012, now Pat. No. 8,614,073, which is a continuation of application No. 12/088,794, filed as application No. PCT/NL2006/000467 on Sep. 21, 2006.

(60) Provisional application No. 60/721,528, filed on Sep. 29, 2005, provisional application No. 60/830,121, filed on Jul. 12, 2006.

(56) References Cited

U.S. PATENT DOCUMENTS

| | | | |
|---|---|---|---|
| 5,955,276 | A | 9/1999 | Morgante et al. |
| 6,013,445 | A | 1/2000 | Albrecht et al. |
| 6,090,556 | A | 7/2000 | Kato |
| 6,100,030 | A | 8/2000 | McCasky Feazel et al. |
| 6,248,526 | B1 | 6/2001 | Weimer |
| 6,480,791 | B1 | 11/2002 | Strathmann |
| 6,534,293 | B1 | 3/2003 | Barany et al. |
| 6,887,666 | B1 | 5/2005 | Hager |
| 7,141,364 | B1 | 11/2006 | Verma et al. |
| 7,217,516 | B2 | 5/2007 | Van Eijk et al. |
| 7,220,549 | B2 | 5/2007 | Buzby |
| 7,300,751 | B2 | 11/2007 | Li et al. |
| 7,323,305 | B2 | 1/2008 | Leamon et al. |
| 7,537,897 | B2 | 5/2009 | Brenner et al. |
| 7,935,488 | B2 | 5/2011 | Zabeau et al. |
| 8,168,385 | B2 | 5/2012 | Brenner |
| 8,614,073 | B2 | 12/2013 | Van Eijk et al. |
| 9,376,719 | B2 | 6/2016 | Eijk et al. |
| 9,574,230 | B2 | 2/2017 | Van Eijk et al. |
| 2002/0025532 | A1 | 2/2002 | Huang et al. |
| 2002/0106649 | A1 | 8/2002 | Lizardi et al. |
| 2002/0198371 | A1 | 12/2002 | Wang |
| 2003/0165923 | A1 | 9/2003 | Li et al. |
| 2003/0190645 | A1 | 10/2003 | Van Eijk et al. |
| 2003/0207279 | A1 | 11/2003 | Crothers et al. |
| 2003/0219767 | A1 | 11/2003 | Ayers et al. |
| 2004/0029155 | A1 | 2/2004 | Rothberg et al. |
| 2004/0053236 | A1 | 3/2004 | McCallum et al. |
| 2004/0081996 | A1 | 4/2004 | Landers et al. |
| 2004/0086912 | A1 | 5/2004 | Luo et al. |
| 2004/0101835 | A1 | 5/2004 | Willis et al. |
| 2004/0157238 | A1 | 8/2004 | Quinn et al. |
| 2004/0185484 | A1 | 9/2004 | Costa et al. |
| 2004/0203032 | A1 | 10/2004 | Lander et al. |
| 2005/0059065 | A1 | 3/2005 | Brenner |
| 2005/0064406 | A1 | 3/2005 | Zabarovsky et al. |
| 2005/0095645 | A1 | 5/2005 | Jones et al. |
| 2005/0130173 | A1 | 6/2005 | Leamon et al. |
| 2005/0153317 | A1 | 7/2005 | Denise et al. |
| 2005/0181408 | A1 | 8/2005 | Brenner |
| 2005/0233354 | A1 | 10/2005 | Kennedy |
| 2006/0177832 | A1 | 8/2006 | Brenner |
| 2006/0177833 | A1 | 8/2006 | Brenner |
| 2007/0020640 | A1 | 1/2007 | McCloskey et al. |
| 2007/0072208 | A1* | 3/2007 | Drmanac ............... C12Q 1/682 435/5 |
| 2008/0032287 | A1 | 2/2008 | Cantor et al. |
| 2008/0194418 | A1 | 8/2008 | Johnson et al. |
| 2009/0005259 | A1 | 1/2009 | Drmanac |
| 2009/0142758 | A1 | 6/2009 | Van Eijk et al. |
| 2009/0208943 | A1 | 8/2009 | Van Eijk et al. |
| 2014/0051585 | A1 | 2/2014 | Prosen et al. |
| 2014/0303007 | A1 | 10/2014 | Van Eijk et al. |
| 2015/0284789 | A1* | 10/2015 | Hogers ............... C12Q 1/6869 506/2 |
| 2017/0137872 | A1 | 5/2017 | Van Eijk et al. |
| 2017/0166962 | A1 | 6/2017 | Van Eijk et al. |
| 2017/0206314 | A1 | 7/2017 | Van Eijk et al. |

FOREIGN PATENT DOCUMENTS

| | | |
|---|---|---|
| EP | 1 124 990 | 8/2001 |
| EP | 1 362 929 A2 | 11/2003 |
| EP | 1 574 585 | 9/2005 |
| EP | 1 634 956 B1 | 3/2006 |
| JP | 2000-041687 | 2/2000 |
| JP | 2002-537855 | 11/2002 |
| JP | 2004-502466 | 1/2004 |
| JP | 2004-113241 | 4/2004 |
| JP | 2004-208586 | 7/2004 |
| JP | 2005-021149 | 1/2005 |
| WO | WO-90/08821 | 8/1990 |
| WO | WO-93/06239 | 4/1993 |
| WO | WO-96/04393 | 2/1996 |
| WO | WO-98/51789 | 11/1998 |
| WO | WO-00/24937 A2 | 5/2000 |
| WO | WO-00/24939 | 5/2000 |
| WO | WO-00/53802 | 9/2000 |
| WO | WO-00/61800 A2 | 10/2000 |
| WO | WO-00/61801 | 10/2000 |
| WO | WO-00/78945 | 12/2000 |
| WO | WO-01/21840 A2 | 3/2001 |
| WO | WO-01/38572 | 5/2001 |
| WO | WO-01/75167 A1 | 10/2001 |
| WO | WO-01/88189 | 11/2001 |
| WO | WO-03/012118 | 2/2003 |
| WO | WO-2004/022758 | 3/2004 |
| WO | WO-2004/057017 | 7/2004 |
| WO | WO-2004/063323 | 7/2004 |
| WO | WO-2005/003375 A2 | 1/2005 |
| WO | WO-2005/065814 | 7/2005 |
| WO | WO-2006/137733 A | 12/2006 |
| WO | WO-2006/137734 | 12/2006 |

OTHER PUBLICATIONS

Margulies Supplementary Information [online] Jul. 31, 2005 [retrieved on Jan. 7, 2018] retrieved from https://www.nature.com/articles/nature03959#supplementary-information (34 pages). (Year: 2005).*

Shendure et al. Next-generation DNA sequencing. Nature Biotechnology 26:1135-1145 (2008). (Year: 2008).*

Accelerated Examination Support Document, filed in the USPTO dated Oct. 5, 2010 in U.S. Appl. No. 12/484,541.

Altshuler, et al. "An SNP map of the human genome generated by reduced representation shotgun sequencing", Nature, Sep. 28, 2000, vol. 47, pp. 513-516.

Amos, CI. et al., "DNA Pooling in Mutation Detection with Reference to Sequence Analysis", American Journal of Human Genetics, vol. 66, 2000, pp. 1689-1692.

Baird, et al. "Rapid SNP Discovery and Genetic Mapping Using Sequenced RAD Markers", PLoS ONE, Oct. 2008, vol. 3, Issue 10, e3376, pp. 1-7.

Bouzidi, et al., "A sunflower BAC library suitable for PCR screening and physical mapping of targeted genomic regions.", TAG, vol. 113, No. 1, 2006, pp. 81-89.

Brenner, et al., "DNA fingerprinting by sampled sequencing", Proc. Natl. Acad. Sci., Nov. 1989, vol. 86, pp. 8902-8906.

(56) References Cited

OTHER PUBLICATIONS

Church, et al., "Multiplex DNA Sequencing", Research Articles, Science, vol. 240, Apr. 1988, pp. 185-188.
Colbert, T. et al., "High-Throughput Screening for Induced Point Mutations", Plant Physiology (2001) vol. 126, pp. 480-484.
English Translation of the Office Action received in the related Japanese Patent Application No. 2008-533267, dated Sep. 26, 2012.
International Search Report for International Application No. PCT/NL2007/000177, dated Nov. 29, 2007. (3 pgs.).
English Translation of the Office Action received in the related Japanese Patent Application No. 2009-504137, dated Aug. 22, 2012.
Office Communication received in the related European Patent Application No. 07747276.9, dated Jan. 15, 2013.
Duprat et al., "The *Arabidopsis* eukaryotic initiation factor (iso) 4E is dispensable for plant growth but required for susceptibility to potyviruses", The Plant Journal, 2002, vol. 32, pp. 927-934.
Epinat et al., "A novel engineered meganuclease induces homologous recombination in yeast and mammalian cells", Nucleic Acids Research, 2003, vol. 31, No. 11, pp. 2952-2962.
European Search Report for European Patent Application No. 10176619, dated Oct. 29, 2010 (3 pages).
Fakhrai-Rad, H. et al., "Prosequencing: An Accurate Detection Platform for Single Nucleotide Polymorphisms", Human Mutation, vol. 19, pp. 479-485 (2002).
First Examination Report in India Appln No. 1142/KOLNP/2008 dated Feb. 17, 2014.
Greene et al., "Spectrum of chemically induced mutations from a large-scale reverse-genetic screen in *Arabidopsis*", Genetics, Jun. 2003, vol. 164, pp. 731-740.
Gregory, et al., "Genome Mapping by Fluorescent Fingerprinting", Genome Research, 1997, vol. 7, pp. 1162-1168.
Gruber, et al. "Estimation of single nucleotide polymorphism allele frequency in DNA pools by using Pyrosequencing", Hum Genet (2002), vol. 110, pp. 395-401.
Gupta, et al. "Single nucleotide polymorphisms: A new paradigm for molecular marker technology and DNA polymorphism detection with emphasis on their use in plants", Current Science, Feb. 25, 2001, vol. 80, No. 4 pp. 524-535.
Havre et al., "Targested mutagenesis of DNA using triple helix-forming oligonucleotides linked to psoralen", Proc. Natl. Acad. Sci, Aug. 1993, vol. 90, pp. 7879-7883.
Henikoff, et al. "TILLING. Traditional Mutagenesis Meets Functional Genomics", Plant Physiology, Jun. 2004, vol. 135, pp. 630-636.
Hug et al., "Measurement of the number of molecules of a single mRNA species in a complex mRNA preparation", J. theor. Biol., 2003, vol. 221, pp. 615-624.
Jamsari, et al., "BAC-derived diagnostic markers for sex determination in asparagus.", Theoretical and Applied Genetics, vol. 108, No. 6, 2004, pp. 1140-1146.
JP 2004-502466 with Wo2002/004672 Trans p. 1.
Klein et al., "A High-throughput AFLP-based Method for Constructing Integrated Genetic and Physical Maps: Progress Toward a Sorghum Genome Map", Genome Research, Jun. 2000, pp. 789-807, I. 10, No. 6, Cold Spring Harbor Laboratory Press.
Klein, et al., "A high-throughput AFLP-based method for constructing integrated genetic and physical maps: Progress toward a sorghum genome map", Genome Research, vol. 10, No. 5, 2000, pp. 789-807.
Lavebratt, et al., "Pyrosequencing-Based SNP Allele Frequency Estimation in DNA Pools", Human Mutation, vol. 23, pp. 92-97 (2004).
Lewis, et al. "High-Density Detection of Restriction-Site-Associated DNA Markers for Rapid Mapping of Mutated Loci in Neurospora", Genetics, Oct. 2007, vol. 177, pp. 1165-1171.
Li et al., "A fast neutron deletion mutagenesis-based reverse genetics system for plants", The Plant Journal, 2001, vol. 27, No. 3, pp. 235-242.
Lloyd et al., "Targeted mutagenesis using zinc-finger nucleases in *Arabidopsis*", PNAS, Feb. 8, 2005, vol. 102, No. 6, pp. 2232-2237.
Margulies et al., "Genome sequencing in microfabricated high-density picolitre reactors", Nature, 2005, vol. 437, pp. 376-380.
Marra, et al., "High Throughput Fingerprint Analysis of Large-Insert Clones", Genome Research, 1997, vol. 7, pp. 1072-1084.
McCallum et al., "Targeting Induced LocalLesions INGenomes (TILLING) for Plant Functional Genomics", Plant Physiology (2000), vol. 123, No. 2, pp. 439-442.
McCallum, et al., "Targeted Screening for Induced Mutations", Nature Biotechnology (Apr. 2000), vol. 18, No. 4, pp. 455-457.
Menda et al., "In silico screening of a saturated mutation library of tomato", The Plant Journal, 2004, vol. 38, pp. 861-872.
Miller et al., "A comprehensive approach to clustering of expressed human gene sequence: the sequence tag alignment and consensus knowledge base", Genome Research, 1999, vol. 9, pp. 1143-1155.
Miller, et al. "RAD marker microarrays enable rapid mapping of zebrafish mutations", Genome Biology, 2007, vol. 8, Issue 6, Article R105, 10 pages.
Miller, et al. "Rapid and cost-effecitve polymorphism identification and genotyping using restriction site associated DNA [RAD] markers", Genome Research, 2007, vol. 17, pp. 240-248.
Nair, et al. "PCR-based DNA markers linked to a gall midge resistance gene, Gm4t, has potential for marker-aided selection in rice", Theor Appl Genet (1996), vol. 92, pp. 660-665.
Nicaise et al., "The eukaryotic translation initiation factor 4E controls lettuce susceptibility to the potyvirus Lettuce mosaic virus1", Plant Physiology, Jul. 2003, vol. 132, pp. 1272-1282.
Notice of Opposition to a European Patent in European Patent No. EP 1929039 by the European Patent Office on Sep. 29, 2010.
PCT International Preliminary Report on Patentability, dated Jan. 13, 2009, 6 pages.
Qiu, F. et al., "DNA Sequence-Based 'Bar Codes' for Tracking the Origins of Expressed Sequence Tags from a Maize eDNA Library Constructed Using Multiple mRNA Sources", Plant Physiology, 133:475-481, Oct. 2003.
Ruffel et al., "A natural recessive resistance gene against potato virus Y in pepper corresponds to the eukaryotic initiation factor 4E (eIF4E)", The Plant Journal, 2002, vol. 32, pp. 1067-1075.
Ruffel et al., "The recessive potyvirus resistance gene pot-1 is the tomato orthologue of the pepper pvr2-eIF4E gene" Mol.Gen. Genetics, 2005, vol. 274, pp. 346-353.
Shendure et al., "Accurate multiplex polony sequencing of an evolved bacterial genome" Science, Sep. 9, 2005, vol. 309, pp. 1728-1732.
Sood, et al., Method for reverse genetic screening in zebrafish by resequencing and TILLING, Methods, vol. 29, 2006, pp. 220-227.
Stemple, D.L., "TILLING—a high-throughput harvest for functional genomics", Nature Reviews | Genetics, vol. 5, pp. 1-6 (Feb. 2004).
Stewart et al., "A rapid CTAB DNA isolation technique useful for RAPD fingerprinting and other PCR applications" Biotechniques, 1993, vol. 14, No. 5., pp. 748-750.
Till, et al. "Large-scale discovery of induced point mutations with high-throughput TILLING." Genome Research, Mar. 2003, vol. 13, No. 3, pp. 524-530.
Vandenbussche, et al. "Toward the analysis of the petunia MADS box gene family by reverse and forward transposon insertion mutagenesis approaches: B, C, and D floral organ identify functions require SEPALLATA-like MADS box genes in petunia." The Plant Cell, Nov. 2003, vol. 15, No. 11, pp. 2680-2693.
Vieux, E. F. et al., "Primer Design for PCR and Sequencing in High-Throughput Analysis of SNPs", BioTechniques, vol. 32, pp. S28-S32 (2002).
Vos, et al., "AFLP: a new technique for DNA fingerprinting", Nucleic Acids Research, 1995, vol. 23, No. 2, pp. 4407-4414.
Wienholds, et al. "Efficient Target-selected mutagenesis in zebrafish." Genome Research, (2003) vol. 13, No. 12, pp. 2700-2707.
Wienholds, et al. "Target-selected gene inactivation in zebrafish", Methods in Cell Biology, 2004, Chapter 4, vol. 77, pp. 69-90.
Wienholds, et al. "Target-Selected Inactivation of the Zebrafish rag1 Gene", Science (2002), vol. 297, pp. 99-102.
Wolford, et al., "High-throughput SNP detection by using DNA pooling and denaturing high performance liquid chromatography (DHPLC)", Human Genetics (2000) vol. 107, pp. 83-487.

(56) References Cited

OTHER PUBLICATIONS

Xia, et al., "Construction and characterization of a BAC library of soybean.", vol. 141, No. 1-2, 2005, pp. 129-137.
U.S. Appl. No. 15/674,126, filed Aug. 10, 2017, Van Eijk et al.
U.S. Appl. No. 15/683,252, filed Aug. 22, 2017, Van Eijk et al.
U.S. Appl. No. 15/729,328, filed Oct. 10, 2017, Van Eijk et al.
U.S. Appl. No. 90/013,467, filed Mar. 13, 2015, Cornell University.
"Instruction Manual AFLP Analysis System 1-7 II AFLP Small Genome Primer Kit", Jan. 22, 2003, retrieved from URL: https://nature.berkeley.edu/brunslab/ftp/aflpii.pdf.
454 Life Science, "Keygene Selects 454 Life Sciences' Novel Sequencing Technology to Enable Large-Scale SNP Discovery and Detection in Higher Eukaryotic Organisms," News & Events—Press Releases, 2006, pp. 1-2, [XP002452166], Internet: URI:http://www.454.com/news-events/press-releases.asp?display=detail&id=46.
Bensch, et al. "Ten years of AFLP in ecology and evolution: why so few animals?", Molecular Ecology, Sep. 2005, vol. 14, Issue 10, pp. 2899-2914.
Bishop, et al. "Analysis of the transcriptome of the protozoan Theileria parva using MPSS reveals that the majority of genes are transcriptionally active in the schizont stage", Nucleic Acids Research, 2005, vol. 33, No. 17, pp. 5503-5511.
Breyne, et al., "Transcriptome analysis during cell division in plants", Proceedings of the National Academy of Sciences, Nov. 2002, vol. 99, No. 23, pp. 14825-14830.
Data sheet Dral, download from the internet, http://www.neb.com/nebecomm/products, printed on Dec. 18, 2010, p. 1.
Dong, et al. "Flexible Use of High-Density Oligonucleotide Arrays for Single-Nucleotide Polymorphism Discovery and Validation", Genome Research, 2001, vol. 11, No. 8, pp. 1418-1424.
Fujiki et al, "Genetic evidence for CFTR dysfunction in Japanese: background for chronic pancreatitis" (2004) J Med Genet, 41, e55, pp. 1-6.
Griffin, et al. "Single-nucleotide polymorphism analysis by MALDI-TOF mass spectrometry", TIBTECH, Feb. 2000, vol. 18, pp. 77-84.
Iwahana, et al. "T-cassette Ligation: A Method for Direct Sequencing and Cloning of PCR-amplified DNA Fragments", PCR Methods and Applications, 1994, pp. 219-224.
Janssen, et al., "Application of Corps? Technology for SNP Marker Discovery in Maize," Plant & Animal Genomes XV Conference, 2007, p. 1 [XP002452171], Internet: URL:http://www.intl-pag.org/15/abstracts/PAG15_PO3e_183.html.
Jordan, et al. "Genome complexity reduction for SNP genotyping analysis", PNAS, Mar. 5, 2002, vol. 99, No. 5, pp. 2942-2947.
Lehninger, "The Principles of Biochemistry", The Johns Hopkins University School of Medicine, Nov. 1982, Table of Contents.
Lindstedt, et al. "A variation fo the amplified-fragment length polymorphism (AFLP) technique using three restriction endonucleases, and assessment of the enzyme combination BgIII-Mfel for AFLP analysis of *Salmonella enterica* subsp. *enterica* isolates", FEMS Microbiology Letters, 2000, vol. 189, pp. 19-24.
Lizardi, et al. "Mutation detection and single-molecule counting using isothermal rolling-circle amplification", Nature Genetics, Jul. 1998, vol. 19, pp. 225-232.
Marth, et al. "A general approach to single-nucleotide polymorphism discovery", Nature Genetics, Dec. 1999, vol. 23, pp. 452-456.
Matsuzaki, et al. "Parallel Genotyping of Over 10,000 SNPs Using a One-Primer Assay on a High-Density Oligonucleotide Array" Genome Research (Mar. 2004) vol. 14, No. 3, pp. 414-425.
Meissner et al., "Reduced representation bisulfite sequencing for comparative high-resolution DNA methylation analysis", Nucleic Acids Research, 2005, vol. 3, No. 18, pp. 5868-5877.
Meksem, K., et al., "Conversion of AFLP bands into high-throughput DNA markers," Mol Genet Genomics, 2001, pp. 207-214, vol. 265.
Meyers, et al. "Analysis of the transcriptional complexity of *Arabidopsis thaliana* by massively parallel signature sequencing", Nature Biotechnology, Aug. 2004, vol. 22, No. 8, pp. 1006-1011.
Mueller, et al. "AFLP genotyping and fingerprinting", Tree (Oct. 1999), vol. 14, No. 10, pp. 389-394.
Nakai, et al. "Highly Multiplexed Genotyping of Coronary Artery Disease-Associated SNPs Using MALDI-TOF Mass Spectrometry", Human Mutation, 2002, vol. 20, pp. 133-138.
Nelson, et al. "Complete Genome Sequence of the Oral Pathogenic Bacterium Porphyromonas gingivalis Strain W83", Journal of Bacteriology, Sep. 2003, pp. 5591-5601.
Nicod, et al. "SNPs by AFLP (SBA): a rapid SNP isolation strategy for non-model organisms", Nucleic Acids Research, 2003, vol. 31, No. 5, e19, 5 pgs.
Rafalski "Applications of single nucleotide polymorphisms in crop genetics", Current Opinion in Plant Biology (2002) vol. 5, pp. 94-100.
Reijans, et al. "Quantitative comparison of cDNA-AFLP, microarrays, and GeneChip expression data in *Saccharomyces cerevisiae*", Genomics, 2003, vol. 82, pp. 606-618.
Retrieved from EBI accession No. UNIPROT:C5Z1DO, Sep. 1, 2009, "RecName: Full=Pectinesterase; EC=3.1.1.11;".
Retrieved from EBI accession No. UNIPROT:Q8VYZ3, Mar. 1, 2002, "RecName: Full=Probable pectinesterase 53; Short=PE 53; EC=3.1.1.11; AltName: Full=Pectin methylesterase 53; short-AtPME53; Flags: Precursor;".
Sallaud, et al. "Highly efficient production and characterization of T-DNA plants for rice (*Oryza sativa* L.) functional genomics", Theor Appl Genet, 2003, vol. 106, pp. 1396-1408.
Savelkoul, et al. "Amplified-Fragment Length Polymorphism Analysis: the State of an Art", Journal of Clinical Microbiology, 1999, vol. 37, No. 10, pp. 3083-3091.
Shendure, et al., "Accurate multiplex polony sequencing of an evolved bacterial genome", Science, Sep. 2005, vol. 309, No. 5741, pp. 1728-1732.
Simko, I. "One potato, two potato: haplotype association mapping in autotetraploids", Trends in Plant Science, vol. 9, No. 9, Sep. 2004, p. 441-448.
Solexa, "Application Note: DNA sequencing," 2006, pp. 1-2, [XP002452169], Internet: URL:http://www.fasteris.com/pdf/DNASeq_AppNote_10_5_06.pdf.
Swindell, "The Association Among Gene Expression Responses to Nine Abiotic Stress Treatments in *Arabidopsis thaliana*", Genetics, Dec. 2006, vol. 1811-1824.
Truong et al, "Sequence-Based Genotyping for Marker Discovery and Co-Dominant Scoring in Germplasm and Populations," May 2012, PLoS ONE, vol. 7, No. 5, e37565, pp. 1-9.
Van Der Meulen, et al. "Highly automated AFLP fingerprint analysis on the MegaBACE capillary sequencer", Plant, Animal & Microbe Genomes X Conference, Jan. 12-16, 2002, P228, pp. 135.
Van Eijk, et al., "Complexity Reduction of Polymorphic Sequences (CRoPS): A Novel Approach for High Throughput Polymorphism Discovery," Plant and Animal Genomes XIV Conference, 2006, p. 1, [XP002452165], Internet: URL:http://www.intl-pag.org/14/abstracts/PAG14_W410.html.
Van Eijk, et al., "Sequence-Based AFLP® Detection Using Solexa's Clonal Single Molecule Array (CSMA?) Technology," Plant & Animal Genomes XV Conference, 2007, p. 1, [XP002452170], Internet: URL:http://www.intl-pag.org/15/abstracts/PAG15_P02c_69.html.
Van Orsouw et al., "Complexity reduction of polymorphic sequences (CRoPS (TM)): A novel approach for large-scale polymorphism discovery in complex genomes", PLoS One, Nov. 2007, vol. 2, No. 11, pp. e1172-e1172, 10 pages.
Volkmuth, et al. "Technical Advances: Genome-Wide cDNA-AFLP Analysis of the *Arabidopsis* Transcriptome", A Journal of Integrative Biology, 2003, vol. 7, No. 2, pp. 143-160.
World's Technology News, "Solexa to Conduct Technology Seminar at the American Society of Human Genetics Conference", 2005, p. 1, [XP002452168], Internet: URL:http://www.mirror99.com/20051028/solexa_to_conduct_technology_seminar_at_the_american_society_of_human_genetics_bhfd.jspx.
Yuanxin, et al. "T-linker-specific ligation PCR (T-linker PCR): an advanced PCR technique for chromosome walking or for isolation of tagged DNA ends", Nucleic Acids Research, 2003, vol. 31, No. 12, e68, 7 pgs.

(56) References Cited

OTHER PUBLICATIONS

Fu et al., "Molecular indexing enables quantitative targeted RNA sequencing and reveals poor efficiencies in standard library preparations", PNAS, Feb. 2014, vol. 111, No. 5, pp. 1891-1896.
Illumina (Data Sheet: Sequencing), www.illimina.com, Pub. No. 770-2012-019, pp. 1-3, first published 2012, current as of Nov. 17, 2014.
Iwahana et al., "T-cassette ligation: A method for direct sequencing and cloning of PCT-amplified DNA fragments", Genome Research, 1994, vol. 3, pp. 219-224.
Miner "Molecular barcodes detect redundancy and contamination in hairpin-bisulfite PCR", Nucleic Acids Research, 2004, vol. 32, No. 17, 4 pages.
Final Office Action issued in U.S. Appl. No. 15/683,252, dated Apr. 6, 2018.
Notice of Allowance issued in U.S. Appl. No. 15/683,252, dated Sep. 14, 2018.

\* cited by examiner

FIG 4 Unique adress for each pool coordinate

METHOD FOR IDENTIFYING THE SOURCE OF AN AMPLICON

CROSS-REFERENCE TO RELATED APPLICATIONS

This application is a Continuation-in-part of U.S. application Ser. No. 15/014,642 filed Feb. 3, 2016, which is a Continuation of U.S. application Ser. No. 14/613,849 filed Feb. 4, 2015, now U.S. Pat. No. 9,284,606, which is a Continuation of U.S. application Ser. No. 14/219,931 filed Mar. 19, 2014, now U.S. Pat. No. 8,975,028, which is a Divisional of U.S. application Ser. No. 13/783,601 filed Mar. 4, 2013, now U.S. Pat. No. 8,685,650, which is a Continuation of U.S. patent application Ser. No. 13/344,162 filed Jan. 5, 2012, now U.S. Pat. No. 8,394,591, which is a divisional of U.S. patent application Ser. No. 12/373,220 filed Mar. 11, 2009, now U.S. Pat. No. 8,178,300, which is a U.S. National Stage of PCT/NL2007/000177 filed Jul. 10, 2007, which claims the benefit of U.S. Provisional Application No. 60/830,121 filed Jul. 12, 2006. The contents of these applications are herein incorporated by reference in their entirety.

This application is also a Continuation-in-part of U.S. application Ser. No. 15/674,126 filed Aug. 10, 2017, which is a Continuation of U.S. patent application Ser. No. 15/434,801 filed Feb. 16, 2017, now U.S. Pat. No. 9,745,627, which is a Continuation of U.S. patent application Ser. No. 15/165,921 filed May 26, 2016, now U.S. Pat. No. 9,574,230, which is a Continuation of U.S. patent application Ser. No. 13/972,152 filed Aug. 21, 2013, now U.S. Pat. No. 9,376,719, which is a Continuation of U.S. patent application Ser. No. 13/447,871 filed Apr. 16, 2012, now U.S. Pat. No. 8,614,073, which is a Continuation of U.S. patent application Ser. No. 12/088,794 filed Sep. 8, 2008, now abandoned, which is a U.S. National Stage of PCT/NL2006/000467 filed Sep. 21, 2006, which claims the benefit of U.S. Provisional Application No. 60/721,528 filed Sep. 29, 2005. The contents of these applications are herein incorporated by reference in their entirety.

SEQUENCE LISTING

The instant application contains a Sequence Listing which has been submitted in ASCII format via EFS-WEB and is hereby incorporated by reference in its entirety. Said ASCII copy, created on Sep. 18, 2017, is named 085342-2000SequenceListing.txt and is 11 KB.

BACKGROUND OF THE INVENTION

Integrated genetic and physical genome maps are extremely valuable for map-based gene isolation, comparative genome analysis and as sources of sequence-ready clones for genome sequencing projects. The effect of the availability of an integrated map of physical and genetic markers of a species for genome research is enormous. Integrated maps allow for precise and rapid gene mapping and precise mapping of microsatellite loci and SNP markers. Various methods have been developed for assembling physical maps of genomes of varying complexity. One of the better characterized approaches use restriction enzymes to generate large numbers of DNA fragments from genomic subclones (Brenner et al., Proc. Natl. Acad. Sci., (1989), 86, 8902-8906; Gregory et al., Genome Res. (1997), 7, 1162-1168; Marra et al., Genome Res. (1997), 7, 1072-1084). These fingerprints are compared to identify related clones and to assemble overlapping clones in contigs. The utility of fingerprinting for ordering large insert clones of a complex genome is limited, however, due to variation in DNA migration from gel to gel, the presence of repetitive DNAs, unusual distribution of restriction sites and skewed clone representation. Most high quality physical maps of complex genomes have therefore been constructed using a combination of fingerprinting and PCR-based or hybridisation based methods. However, one of the disadvantages of the use of fingerprinting technology is that it is based on fragment-pattern matching, which is an indirect method.

It would be preferred to create physical maps by generating the contigs based on actual sequence data, i.e. a more direct method. A sequence-based physical map is not only more accurate, but at the same time also contributes to the determination of the whole genome sequence of the species of interest. Recently methods for high throughput sequencing have been made available that would allow for the determination of complete nucleotide sequences of clones in a more efficient and cost-effective manner.

However, detection by sequencing of the entire restriction fragment is still relatively uneconomical. Furthermore, the current state of the art sequencing technology such as disclosed herein elsewhere (from 454 Life Sciences, www.454.com, Solexa, www.solexa.com, and Helicos, www.helicosbio.com), despite their overwhelming sequencing power, can only provide sequencing fragments of limited length. Also the current methods do not allow for the simultaneous processing of many samples in one run.

Further, populations carrying mutations, either induced or naturally occurring are used in modern genomics research to identify genes affecting traits of importance by reverse genetics approaches. This is in particular applicable for plants and crops of agronomic importance, but such populations are also useful, for other organisms such as yeast, bacteria etc. Other organisms, such as animals, birds, mammals etc can also be used, but these populations are typically more cumbersome to obtain or to control. Nevertheless, it is observed that the invention described herein is of a very general nature, and can be applied also to such organisms. Mutagenized populations represent complementary tools for gene discovery, as such populations are commonly used to screen known genes for loss-of-function mutations or assessing phenotype changes in organisms with the mutated gene. The rate-limiting step is the screening work associated with identification of, respectively, organisms carrying a mutation in the gene of interest.

Mutations are lighter, sequence errors darker colored. Plant IDs are known for mutations identified by 3 tags (1, 2, 3) and (4, 5, 6) but not for those identified by less than 2 tag (7,8). Sequence errors are expected to be observed randomly and just once.

Figure 8:
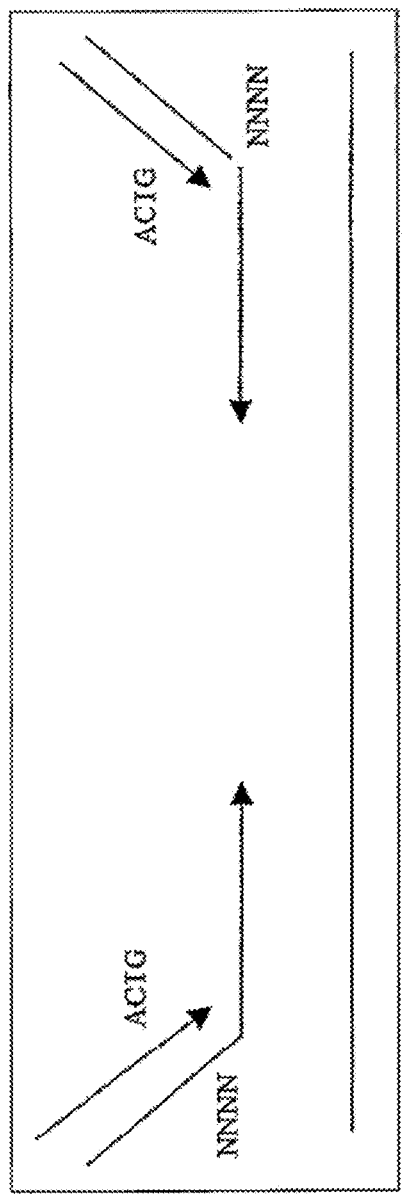

FIG. 8: Illustration of the system of long and short PCR primers to use in tagging the sequences.

Figure 9:
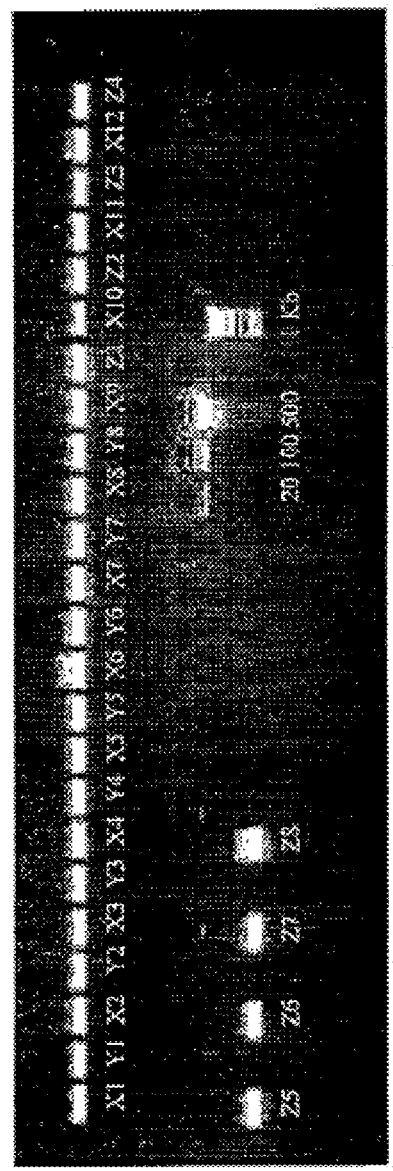

FIG. 9: Agarose gel estimation of the PCR amplification yield of eIF4E exon 1 amplification for each of the 28 3D pools.

DEFINITIONS

In the following description and examples a number of terms are used. In order to provide a clear and consistent understanding of the specification and claims, including the scope to be given such terms, the following definitions are provided. Unless otherwise defined herein, all technical and scientific terms used have the same meaning as commonly understood by one of ordinary skill in the art to which this invention belongs. The disclosures of all publications, patent applications, patents and other references are incorporated herein in their entirety by reference.

Nucleic acid: a nucleic acid according to the present invention may include any polymer or oligomer of pyrimidine and purine bases, preferably cytosine, thymine, and uracil, and adenine and guanine, respectively (See Albert L. Lehninger, Principles of Biochemistry, at 793-800 (Worth Pub. 1982) which is herein incorporated by reference in its entirety for all purposes). The present invention contemplates any deoxyribonucleotide, ribonucleotide or peptide nucleic acid component, and any chemical variants thereof, such as methylated, hydroxymethylated or glycosylated forms of these bases, and the like. The polymers or oligomers may be heterogenous or homogenous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

AFLP: AFLP refers to a method for selective amplification of nucleic acids based on digesting a nucleic acid with one or more restriction endonucleases to yield restriction fragments, ligating adaptors to the restriction fragments and amplifying the adaptor-ligated restriction fragments with at least one primer that is (in part) complementary to the adaptor, (in part) complementary to the remains of the restriction endonuclease, and that further contains at least one randomly selected nucleotide from amongst A, C, T, or G (or U as the case may be). AFLP does not require any prior sequence information and can be performed on any starting DNA. In general, AFLP comprises the steps of:
  (a) digesting a nucleic acid, in particular a DNA or cDNA, with one or more specific restriction endonucleases, to fragment the DNA into a corresponding series of restriction fragments;
  (b) ligating the restriction fragments thus obtained with a double-stranded synthetic oligonucleotide adaptor, one end of which is compatible with one or both of the ends of the restriction fragments, to thereby produce adaptor-ligated, preferably tagged, restriction fragments of the starting DNA;
  (c) contacting the adaptor-ligated, preferably tagged, restriction fragments under hybridizing conditions with one or more oligonucleotide primers that contain selective nucleotides at their 3'-end;
  (d) amplifying the adaptor-ligated, preferably tagged, restriction fragment hybridised with the primers by PCR or a similar technique so as to cause further elongation of the hybridised primers along the restriction fragments of the starting DNA to which the primers hybridised; and
  (e) detecting, identifying or recovering the amplified or elongated DNA fragment thus obtained.

AFLP thus provides a reproducible subset of adaptor-ligated fragments. AFLP is described in inter alia EP 534858, U.S. Pat. No. 6,045,994 and in Vos et al. (Nucleic Acid Research, 1995, 23, 21, 4407-4414) Reference is made to these publications for further details regarding AFLP. The AFLP is commonly used as a complexity reduction technique and a DNA fingerprinting technology. Within the context of the use of AFLP as a fingerprinting technology, the concept of an AFLP marker has been developed.

Selective base: located at the 3' end of the primer that contains a part that is complementary to the adaptor and a part that is complementary to the remains of the restriction site, the selective base is randomly selected from amongst A, C, T or G. By extending a primer with a selective base, the subsequent amplification will yield only a reproducible subset of the adaptor-ligated restriction fragments, i.e. only the fragments that can be amplified using the primer carrying the selective base. Selective nucleotides can be added to the 3' end of the primer in a number varying between 1 and 10. Typically 1-4 suffice and are preferred. Both primers may contain a varying number of selective bases. With each added selective base, the number of amplified adaptor-ligated restriction fragments (amplicons) in the subset is reduced by a factor of about 4. Typically, the number of selective bases used in AFLP is indicated by +N+M, wherein one primer carries N selective nucleotides and the other primers carries M selective nucleotides. Thus, an Eco/Mse+1/+2 AFLP is shorthand for the digestion of the starting DNA with EcoRI and MseI, ligation of appropriate adaptors and amplification with one primer directed to the EcoRI restricted position carrying one selective base and the other primer directed to the MseI restricted site carrying 2 selective nucleotides. A primer used in AFLP that carries at least one selective nucleotide at its 3' end is also depicted as an AFLP-primer. Primers that do not carry a selective nucleotide at their 3' end and which in fact are complementary to the adaptor and the remains of the restriction site are sometimes indicated as AFLP+0 primers.

Clustering: with the term "clustering" is meant the comparison of two or more nucleotide sequences based on the presence of short or long stretches of identical or similar nucleotides and grouping together the sequences with a certain minimal level of sequence homology based on the presence of short (or longer) stretches of identical or similar sequences.

Assembly: construction of a contig based on ordering a collection of (partly) overlapping sequences, also called "contig building".

Alignment: positioning of multiple sequences in a tabular presentation to maximize the possibility for obtaining regions of sequence identity across the various sequences in the alignment, e.g. by introducing gaps. Several methods for alignment of nucleotide sequences are known in the art, as will be further explained below.

Identifier: a short sequence that can be added an adaptor or a primer or included in its sequence or otherwise used as label to provide a unique identifier. Such a sequence identifier (tag) can be a unique base sequence of varying but defined length uniquely used for identifying a specific nucleic acid sample. For instance 4 bp tags allow 4(exp4) =256 different tags. Typical examples are ZIP sequences, known in the art as commonly used tags for unique detection by hybridization (Iannone et al. Cytometry 39:131-140, 2000). Using such an identifier, the origin of a PCR sample can be determined upon further processing. In the case of combining processed products originating from different nucleic acid samples, the different nucleic acid samples are generally identified using different identifiers.

Sequencing: The term sequencing refers to determining the order of nucleotides (base sequences) in a nucleic acid sample, e.g. DNA or RNA.

High-throughput screening: High-throughput screening, often abbreviated as HTS, is a method for scientific experimentation especially relevant to the fields of biology and chemistry. Through a combination of modern robotics and other specialised laboratory hardware, it allows a researcher to effectively screen large amounts of samples simultaneously.

Restriction endonuclease: a restriction endonuclease or restriction enzyme is an enzyme that recognizes a specific nucleotide sequence (target site) in a double-stranded DNA molecule, and will cleave both strands of the DNA molecule at or near every target site.

Restriction fragments: the DNA molecules produced by digestion with a restriction endonuclease are referred to as restriction fragments. Any given genome (or nucleic acid, regardless of its origin) will be digested by a particular restriction endonuclease into a discrete set of restriction fragments. The DNA fragments that result from restriction endonuclease cleavage can be further used in a variety of techniques and can for instance be detected by gel electrophoresis.

Ligation: the enzymatic reaction catalyzed by a ligase enzyme in which two double-stranded DNA molecules are covalently joined together is referred to as ligation. In general, both DNA strands are covalently joined together, but it is also possible to prevent the ligation of one of the two strands through chemical or enzymatic modification of one of the ends of the strands. In that case the covalent joining will occur in only one of the two DNA strands.

Synthetic oligonucleotide: single-stranded DNA molecules having preferably from about 10 to about 50 bases, which can be synthesized chemically are referred to as synthetic oligonucleotides. In general, these synthetic DNA molecules are designed to have a unique or desired nucleotide sequence, although it is possible to synthesize families of molecules having related sequences and which have different nucleotide compositions at specific positions within the nucleotide sequence. The term synthetic oligonucleotide will be used to refer to DNA molecules having a designed or desired nucleotide sequence.

Adaptors: short double-stranded DNA molecules with a limited number of base pairs, e.g. about 10 to about 50 base pairs in length, which are designed such that they can be ligated to the ends of restriction fragments. Adaptors are generally composed of two synthetic oligonucleotides which have nucleotide sequences which are partially complementary to each other. When mixing the two synthetic oligonucleotides in solution under appropriate conditions, they will anneal to each other forming a double-stranded structure. After annealing, one end of the adaptor molecule is designed such that it is compatible with the end of a restriction fragment and can be ligated thereto; the other end of the adaptor can be designed so that it cannot be ligated, but this need not be the case (double ligated adaptors).

Adaptor-ligated restriction fragments: restriction fragments that have been capped by adaptors.

Primers: in general, the term primers refer to DNA strands which can prime the synthesis of DNA. DNA polymerase cannot synthesize DNA de novo without primers: it can only extend an existing DNA strand in a reaction in which the complementary strand is used as a template to direct the order of nucleotides to be assembled. We will refer to the synthetic oligonucleotide molecules which are used in a polymerase chain reaction (PCR) as primers.

DNA amplification: the term DNA amplification will be typically used to denote the in vitro synthesis of double-stranded DNA molecules using PCR. It is noted that other amplification methods exist and they may be used in the present invention without departing from the gist.

"TILLING" or "Targeting induced local lesions in genomes" is a general reverse genetic strategy providing an allelic series of induced (point) mutations by random chemical or physical mutagenesis in combination with PCR-based screening to identify point mutations in a region of interest. In TILLING screening, regions of interest are amplified by PCR. Heteroduplexes between wild-type fragments and fragments harboring an induced mutation are formed by denaturing and reannealing PCR products. These heteroduplexes are cleaved by CEL I and cleaved products are resolved. Throughput can be increased by pooling. Following discovery of PCR products harboring sequence differences in a pool, PCR products included in the pool are commonly screened again by Sanger sequencing of individual PCR products, thereby identifying the mutant plant and the exact sequence difference in the mutated gene.

"Mutagenized Population" refers to a population of organisms (usually plants, but other organisms, including animals such as *Drosophila* and mice may be used to create a mutagenized populations; Schimenti et al., 1998, *Genome Research* 8:698-710) that have been subjected to mutagenesis (chemical or physical) to yield a library of mutants. TILLING populations may vary widely in size, and for certain purposes, partial TILLING populations can be used that contain 90, 80 70, 60, 50, 40 30 or even only 20% of the original population. As an alternative to mutagenized populations, populations can be used wherein the population is not mutagenized but comprises sub-populations that contain naturally occurring mutations such as Single nucleotide polymorphisms (SNPs), small insertions and deletions, and variations in microsatellite repeat number. These populations are particularly advantageous when mutagenized populations are not readily accessible (humans) or where already large germplasms are available. See for instance Comai et al., The Plant Journal, 2004, 37, 778-786. Such a population can be used in combination with a 'reference DNA'.

"Targeted Nucleotide Exchange" or "TNE". Targeted nucleotide exchange (TNE) is a process by which a synthetic oligonucleotide, partially complementary to a site in a chromosomal or an episomal gene directs the reversal of a single nucleotide at a specific site. THE has been described using a wide variety of oligonucleotides and targets. Some of the reported oligonucleotides are RNA/DNA chimeras, contain terminal modifications to impart nuclease resistance.

"Region targeted mutagenesis" or "RTM". Region targeted mutagenesis is a process by which double-strand breaks at a predefined target site in the genomic DNA are artificially created, resulting in repair of the break by one of various available cellular repair mechanisms, mostly leading to mutations at the site of the break. Double-strand breaks may be created by introduction into the cell nucleus of zinc-finger nucleases (e.g. see Lloyd et al., 2005), meganucleases such as I-SceI (Epinat et al., 2003), or triplex-forming oligonucleotides coupled to mutagenic chemical groups (Havre et al., 1993).

"Tagging" refers to the addition of a tag or label to a nucleic acid in order to be able to distinguish it from a second or further nucleic acid. Tagging can be performed, for example, by the addition of a sequence identifier during amplification by using tagged primers or by any other means known in the art. Such a sequence identifier can be a unique base sequence of varying but defined length uniquely used for identifying a specific nucleic acid sample. Typical example are ZIP sequences. Using such a tag, the origin of a sample can be determined upon further processing. In the case of combining processed products originating from different nucleic acid samples, the different nucleic acid samples are generally identified using different tags.

"Tagged library" refers to a library of tagged nucleic acids.

"Primers with increased affinity" are primers with modified nucleotides such as PNA or LNA, which increases their thermal stability and allows for allele-specific amplification based on single nucleotide sequence differences. In order to achieve this, one or several modified nucleotides are often included, preferably at the 3'-end of the primer.

"DNA amplification" is typically used to denote the in vitro synthesis of double-stranded DNA molecules using PCR. It is noted that other amplification methods exist and they may also be used in the present invention.

DETAILED DESCRIPTION OF THE INVENTION

In one aspect, the invention relates to a method for the generation of a physical map of at least part of a genome comprising the steps of:
(a) providing a sample DNA;
(b) generating an artificial chromosome (BAC, YAC) clone bank wherein each artificial chromosome clone contains part of the sample DNA;
(c) combining the artificial chromosome clones in one or more pools, wherein each clone is present in more than one pool, to create a library;
(d) digesting the DNA of one or more pools with one or more restriction endonucleases to provide for a set of restriction fragments for each pool;
(e) ligating adaptors to one or both sides of the restriction fragments, wherein at least one adaptor contains a pool-specific identifier or a degenerate identifier section, respectively, to provide adaptor-ligated restriction fragments;
(f) optionally, combining the adaptor-ligated restriction fragments;
(g) amplifying the adaptor-ligated restriction fragments of step (e) with at least one primer, which primer contains a pool-specific section corresponding to the pool-specific identifier section in the adaptor or contains a pool-specific identifier at the position of the degenerate identifier section, respectively, to provide tagged amplified adaptor-ligated restriction fragments (amplicons);
(h) optionally, combining the amplicons in a set of combined amplicons;
(i) determining the sequence of at least the pool-specific identifier and part of the restriction fragment of the amplicons or set of combined amplicons;
(j) assigning the restriction fragment sequences determined in the amplicons of step (i) to the corresponding clones using the pool-specific identifiers;
(k) ordering the restriction fragments derived from the same clone to build a contig;
(l) ordering the contigs of the clones of step (k) to thereby build a clone-contig and generate a physical map.

In step (a) of the method a sample DNA is provided. This can be achieved by any means in the art such as disclosed for instance by Sambrook et al (Sambrook and Russell (2001) "Molecular Cloning: A Laboratory Manual ($3^{rd}$ edition), Cold Spring Harbor Laboratory, Cold Spring Harbor Laboratory Press). The sample DNA can be from any species, in particular from human, plant or animal origin. It is possible to use only a part of a genome, but that is not necessary as the present invention also provides for methods to accommodate genomes of any size, for instance through the creation of reproducible subsets via selective amplification based on AFLP, as described herein elsewhere. Thus typically, the present method uses the entire genome.

In step (b) an artificial clone bank is generated. The library can be a Bacterial Artificial Chromosome library (BAC) or based on yeast (YAC). Other libraries such as based on cosmids, PAC, TAC or MAC are also possible. Preferred is a BAC library. The library is preferably of a high quality and preferably is a high insert size genomic library. This means that the individual BAC contains a large insert of the genomic DNA under investigation (typically >125 kbp). The size of the preferred large insert is species-dependent. Throughout this application reference is made to BACs as examples of artificial chromosomes. However, it is noted that the present invention is not limited thereto and that other artificial chromosomes can be used without departing from the gist of the invention. Preferably the libraries contain at least five genome equivalents, more preferably at least 7, most preferably at least 8. Particularly preferred is at least 10. The higher the number of genome equivalents in the library, the more reliable the resulting contigs and physical map will be.

The individual clones in the library are pooled to form pools containing a multitude of artificial chromosomes or clones. The pooling may be the simple combination of a number of individual clones into one sample (for example, 100 clones into 10 pools, each containing 10 clones), but also more elaborate pooling strategies may be used. The distribution of the clones over the pools is preferably such that each clone is present in at least two or more of the pools. Preferably, the pools contain from 10 to 10000 clones per pool, preferably from 100 to 1000, more preferably from 250 to 750. It is observed that the number of clones per pool can vary widely, and this variation is related to, for instance, the size of the genome under investigation. Typically, the maximum size of a pool or a sub-pool is governed by the ability to uniquely identify a clone in a pool by a set of identifiers. As will be further elaborated on hereinbelow, a typical range for a genome equivalent in a pool is in the order of 0.2-0.3, and this may again vary per genome. The pools are generated based on pooling strategies well known in the art. The skilled man is capable selecting the optimal pooling strategy based on factors such as genome size etc. The resulting pooling strategy will depend on the circumstances, and examples thereof are plate pooling, N-dimensional pooling such as 2D-pooling, 3D-pooling, 6D-pooling or complex pooling. To facilitate handling of large numbers of pools, the pools may, on their turn, be combined in super-pools (i.e. super-pools are pools of pools of clones) or divided into subpools, as is exemplified in the appending FIG. 1 where a 3D pooling is illustrated. Other examples of pooling strategies and their deconvolution (i.e. the correct identification of the individual clone in a library by detection of the presence of an known associated indicator (i.e. label or identifier) of the clone in one or more pools or subpools) are for instance described in U.S. Pat. No. 6,975,943 or in Klein et al. in Genome Research, (2000), 10, 798-807. The pooling strategy is preferably such that every clone in the library is distributed such over the pools that a unique combination of pools is made for every clone. The result thereof is that a certain combination of (sub)pools uniquely identifies a clone.

The pools are digested with restriction endonucleases to yield restriction fragments. Each pool is preferably separately subjected to an endonuclease digest. Each pool is treated with the same (combination of) endonuclease(s). In principle any restriction endonuclease can be used. Restriction endonucleases may be frequent cutters (4 or 5 cutters, such as MseI or PstI) or rare cutters (6 and more cutters such as EcoRI, HindIII). Typically, restriction endonucleases are selected such that restriction fragments are obtained that are, on average, present in an amount or have a certain length distribution that is adequate for the subsequent steps. In certain embodiments, two or more restriction endonucleases can be used and in certain embodiments, combinations of rare and frequent cutters can be used. For large genomes the use of, for instance, three or more restriction endonucleases can be used advantageously.

To one or both ends of the restriction fragments, adaptors are ligated in step (e) to provide for adaptor-ligated restriction fragments. Typically, adaptors are synthetic oligonucleotides as defined herein elsewhere. The adaptors used in the present invention preferably contain an identifier section, in essence as defined herein elsewhere. In certain embodiments, the adaptor contains a pool-specific identifier, i.e. for each pool, an adapter containing a unique identifier is used that unequivocally indicates the pool. In certain embodiments, the adaptor contains a degenerate identifier section which is used in combination with a primer containing a pool-specific identifier.

In certain embodiments, the adapter-ligated restriction fragments can be combined in larger groups, in particular when the adaptors contain a pool-specific identifier. This combination in larger groups may aid in reducing the number of parallel amplifications of each set of adapter-ligated restriction fragments obtained from a pool.

The adaptor-ligated restriction fragments can be amplified using a set of primers of which at least one primer contains a pool-specific identifier at the position of the pool-specific or degenerate identifier in the adaptor. This embodiment also allows for the grouping of adaptor-ligated restriction fragments prior to the amplification as outlined above. In an alternative embodiment, each pool of adaptor-ligated restriction fragments, wherein the adaptor contained a degenerate identifier section, is amplified separately using a set of primers of which at least one primer contains a pool specific section, thereby uniquely identifying the pool.

Either way, the result is a set of amplified adapter-ligated restriction fragments, also depicted as amplicons, that are linked to the pool from which they originate by the presence in the amplicon of the pool-specific identifier. In certain embodiments, sub-sets of amplicons may be created by selective amplification using primers carrying selective nucleotides at their 3' end, essentially as described herein elsewhere.

The amplicons may be combined in certain embodiments, in a set of combined amplicons or a so-called sequence library.

In step (i) of the method, the amplicons are subjected to sequencing, preferably high throughput sequencing as described herein below. During sequencing, at least part of the nucleotide sequence of the amplicons is determined. Preferably at least the sequence of the pool-specific identifier and part of the restriction fragment of the amplicons is determined. Preferably, a sequence of at least 10 nucleotides of the restriction fragment is determined. In certain embodiments, at least 11, 12, 13, 14 or 15 nucleotides of the restriction fragment are determined. The number of nucleotides that are to be determined minimally will be, again, genome dependent. For instance, in plants more repetitive sequences are present, hence longer sequences (25-30 bp) are to be determined. For instance, calculations on the known genome of Arabidopsis have shown that, when including a 6 bp restriction site in the sequencing step, about 20 bp per restriction fragment needs to be determined. It is possible to determine the sequence of the entire restriction fragment, but this is not an absolute necessity for contig building of a BAC clone.

In the sequencing step, to provide for increased accuracy, the sequence library may be sequenced with a coverage of at least 5. This means that the sequence is determined of at least 5 amplicons obtained from the amplification of one specific adaptor-ligated restriction fragment. In other words: each restriction fragment is (statistically) sequenced at least five times. Increased coverage is preferred as its improves accuracy further, so preferably coverage is at least 7, more preferably a least 10. Increased coverage is used to compensate for a phenomenon that is known as 'sampling variation'.

In the following step, the (partly) sequenced amplicons are correlated to the corresponding clone, typically in silico by means of computerized methods. The amplicons are selected that contain identical sections of nucleotides in the restriction fragment-derived part. Subsequently the different pool-specific identifiers are identified that are present in those amplicons. The combination of the different pool-specific identifiers and hence the sequence of the restriction fragment can be uniquely assigned to a specific clone (a process described earlier as 'deconvolution'). For example, in the case of a 3D pooling strategy (X,Y,Z), each pool in the library is uniquely addressed by a combination of 3 pool-specific identifiers. Each clone occurs more than once in the library, so for each occurrence of a clone in the library, a combination of 3 pool-specific identifiers can be made in combination with the same restriction fragment-derived section. In other words: a restriction fragment-derived section originating from a clone will be tagged with 3 different identifiers. Unique restriction fragment-derived sections, when observed in combination with the 3 identifiers can be assigned to a single BAC clone. This can be repeated for each amplicon that contains other unique sections of nucleotides in the restriction fragment-derived part. This process of deconvolution can be made easier by keeping the genome equivalent per pool relatively low (<0.3, pref. 0.2), thereby reducing the chance that the same fragment is present twice in the same pool derived from different clones.

Figure 1:
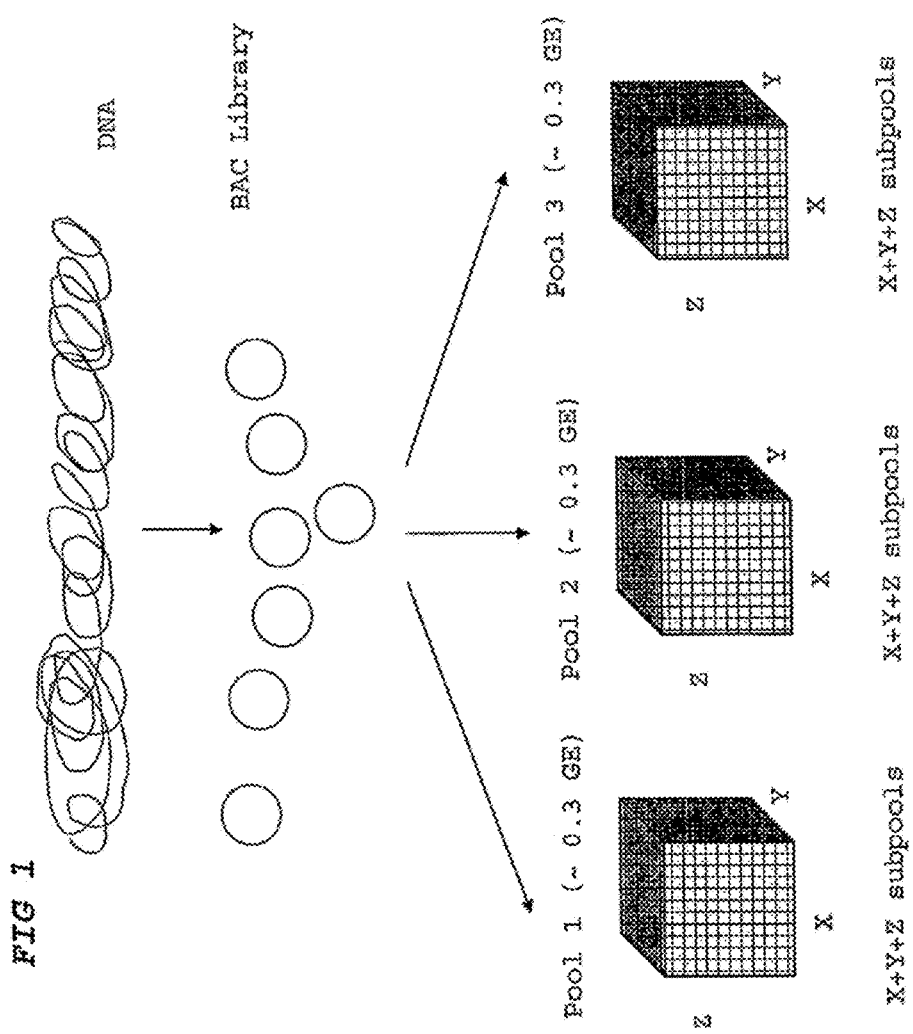
FIG. 1: Schematic representation of pooling strategies.
Figure 2:
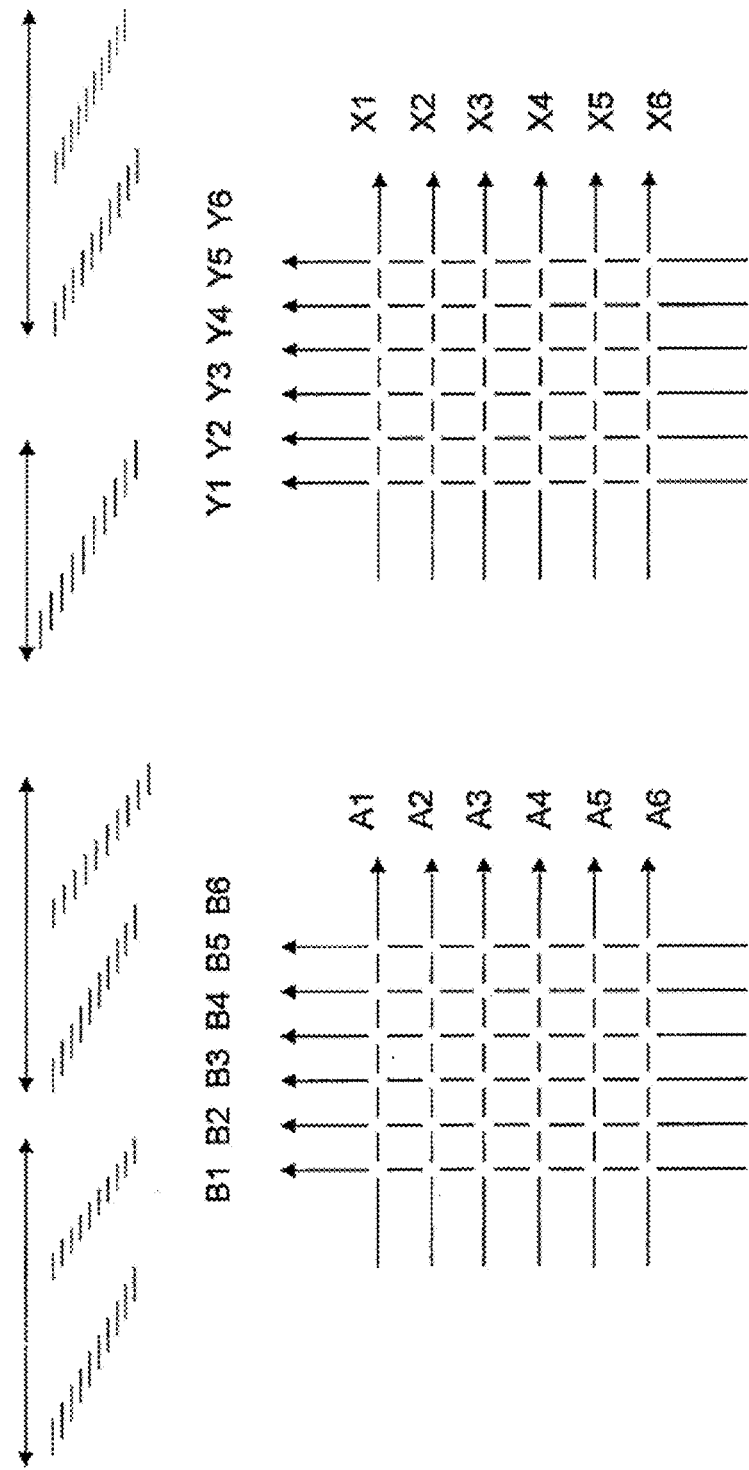
FIG. 2: Four continuous BAC-contigs on *Arabidopsis* chromosome 4—pooling strategy
Figure 3:
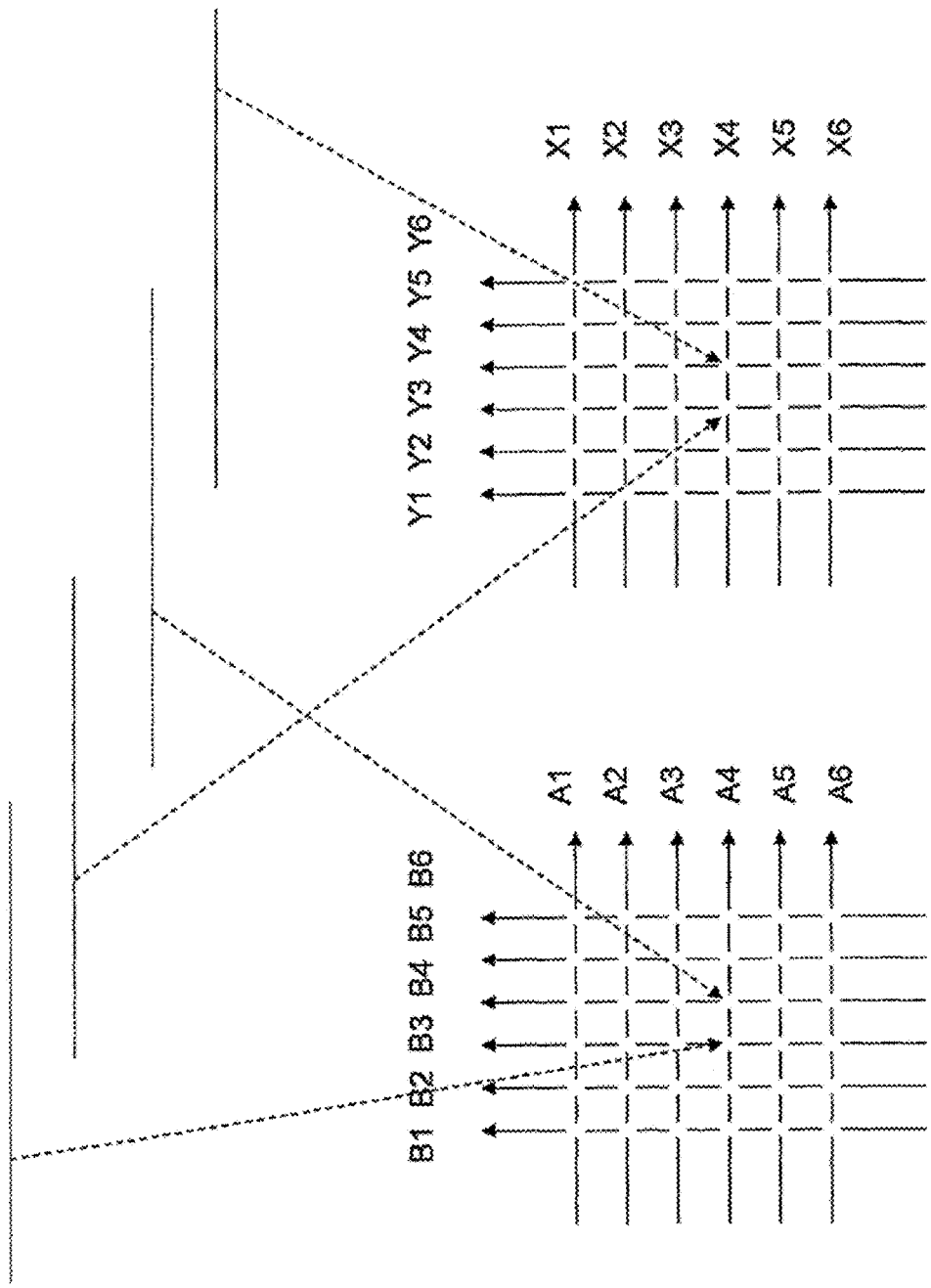
FIG. 3: No overlaps within the group, alternating minimal tiling path

An exemplary representation of the pooling concept is provided in FIG. 1. A sample DNA is converted into BAC library. The BAC library is pooled in a set of pools (M) (3 pools are shown, each containing about 0.3 GE,). Each pool is divided into (X+Y+Z) subpools (typically a stack of microtiterplates).

The sequenced amplicons that are now linked to a particular clone in the library are used in building a contig based on sequence matching of the restriction fragment derived sections. The contigs of each clone are then aligned to generate a physical map.

The advantages of the present method reside inter alia in the improved accuracy for BAC contig building compared to conventional technology for BAC contig building. Furthermore, physical map building based on sequence information is more accurate, as it is a direct way of physical map construction and contributes to the determination of the genome sequence, and further contributes sequence information suitable for STS development and comparative mapping purposes.

The high throughput sequencing used in the present invention is a method for scientific experimentation especially relevant to the fields of biology and chemistry. Through a combination of modern robotics and other specialised laboratory hardware, it allows a researcher to effectively screen large amounts of samples simultaneously.

It is preferred that the sequencing is performed using high-throughput sequencing methods, such as the methods disclosed in WO 03/004690, WO 03/054142, WO 2004/069849, WO 2004/070005, WO 2004/070007, and WO 2005/003375 (all in the name of 454 Life Sciences), by Seo et al. (2004) Proc. Natl. Acad. Sci. USA 101:5488-93, and technologies of Helicos, Solexa, US Genomics, etcetera, which are herein incorporated by reference.

454 Life Sciences Technology

In certain embodiments, it is preferred that sequencing is performed using the apparatus and/or method disclosed in WO 03/004690, WO 03/054142, WO 2004/069849, WO 2004/070005, WO 2004/070007, and WO 2005/003375 (all in the name of 454 Life Sciences), which are herein incorporated by reference. The technology described allows sequencing of 20 to 40 million bases in a single run and is 100 times faster and cheaper than competing technology. The sequencing technology essentially contains 5 steps: 1) fragmentation of DNA and ligation of specific adaptors to create a library of single-stranded DNA (ssDNA); 2) annealing of ssDNA to beads, emulsification of the beads in water-in-oil microreactors and performing emulsion PCR to amplify the individual ssDNA molecules on beads; 3) selection of/enrichment for beads containing amplified ssDNA molecules on their surface 4) deposition of DNA carrying beads in a PicoTiter™ Plate; and 5) simultaneous sequencing in 100,000 wells by generation of a pyrophosphate light signal. The method will be explained in more detail below.

In a preferred embodiment, the sequencing comprises the steps of:
  a. annealing adapted fragments to beads, each bead being annealed with a single adapted fragment;
  b. emulsifying and amplifying the annealed fragments on the beads in water-in-oil microreactors, each water-in-oil microreactor comprising a single bead;
  c. loading the beads in wells, each well comprising a single bead; and generating a pyrophosphate signal.

In the first step (a), sequencing adaptors are ligated to fragments within the combination library. Said sequencing adaptor includes at least a region for annealing to a complementary oligonucleotide bound to a bead, a sequencing primer region and a PCR primer region. Thus, adapted fragments are obtained.

In the first step, adapted fragments are annealed to the beads, each bead annealing with a single adapted fragment. To the pool of adapted fragments, beads are added in excess as to ensure annealing of one single adapted fragment per bead for the majority of the beads (Poisson distribution). In the present invention, the adapters that are ligated to the restriction fragments obtained from the clones may comprise a section that is capable of annealing to a bead.

In a next step, the beads are emulsified in water-in-oil microreactors, each water-in-oil microreactor comprising a single bead. PCR reagents are present in the water-in-oil microreactors allowing a PCR reaction to take place within the microreactors. Subsequently, the microreactors are broken, and the beads comprising DNA (DNA positive beads) are enriched, i.e. separated from beads not containing amplified fragments.

In a following step, the enriched beads are loaded in wells, each well comprising a single bead. The wells are preferably part of a PicoTiter™ Plate allowing for simultaneous sequencing of a large number of fragments.

After addition of enzyme-carrying beads, the sequence of the fragments is determined using pyrosequencing. In successive steps, the PicoTiter™ Plate and the beads as well as the enzyme beads therein are subjected to different deoxyribonucleotides in the presence of conventional sequencing reagents, and upon incorporation of a deoxyribonucleotide a light signal is generated which is recorded. Incorporation of the correct nucleotide will generate a pyrosequencing signal which can be detected.

Pyrosequencing itself is known in the art and described inter alia on www.biotagebio.com; www.pyrosequencing.com/section technology. The technology is further applied in e.g. WO 03/004690, WO 03/054142, WO 2004/069849, WO 2004/070005, WO 2004/070007, and WO 2005/003375 (all in the name of 454 Life Sciences), and Margulies et al., nature 2005, 437, 376-380, which are herein incorporated by reference.

In the present invention, the beads are preferably equipped with primer sequences or parts thereof that are capable of being extended by polymerisation to yield bead-bound amplicons. In other embodiments, the primers used in the amplification are equipped with sequences, for instance at their 5'-end, that allow binding of the amplicons to the beads in order to allow subsequent emulsion polymerisation followed by sequencing. Alternatively, the amplicons may be ligated with sequencing adaptors prior to ligation to the beads or the surface. The sequenced amplicons will reveal the identity of the identifier and hence the combination of identifiers reveals the identity of the clone.

Solexa Technologies

One of the methods for high throughput sequencing is available from Solexa, United Kingdom (www.solexa.co.uk) and described inter alia in WO0006770, WO0027521, WO0058507, WO0123610, WO0157248, WO0157249, WO02061127, WO03016565, WO03048387, WO2004018497, WO2004018493, WO2004050915, WO2004076692, WO2005021786, WO2005047301, WO2005065814, WO2005068656, WO2005068089, WO2005078130. In essence, the method starts with adaptor-ligated fragments of DNA, in this particular case of adapter-ligated restriction fragments of the artificial chromosome pools as described herein elsewhere. The adaptor-ligated DNA is randomly attached to a dense lawn of primers that are attached to a solid surface, typically in a flow cell. The other end of the adaptor ligated fragment hybridizes to a complementary primer on the surface. The primers are extended in the presence of nucleotides and polymerases in a so-called solid-phase bridge amplification to provide double stranded fragments. This solid phase bridge amplification may be a selective amplification. Denaturation and repetition of the solid-phase bridge amplification results in dense clusters of amplified fragments distributed over the surface. The sequencing is initiated by adding four differently labelled reversible terminator nucleotides, primers and polymerase to the flow cell. After the first round of primer extension, the labels are detected, the identity of the first incorporated bases is recorded and the blocked 3' terminus and the fluorophore are removed from the incorporated base. Then the identity of the second base is determined in the same way and so sequencing continues.

In the present invention, the adaptor-ligated restriction fragments or the amplicons are bound to the surface via the primer binding sequence or the primer sequence. The sequence is determined as outlined, including the identifier sequence and (part of) the restriction fragment. Currently available Solexa technology allows for the sequencing of fragments of about 25 base pairs. By economical design of the adaptors and the surface bound primers, the sequencing step reads through the sample identifier, the remains of the recognition sequence of the restriction endonuclease and any optional selective bases. When a 6 bp sample identifier is used, the remains are from the rare cutter EcoRI (AACCT), the use of two selective bases yields an internal sequence of the restriction fragment of 12 bp that can be used to uniquely identify the restriction fragment in the sample.

In a preferred embodiment based on the Solexa sequencing technology above, the amplification of the adapter ligated restriction fragments is performed with a primer that contains at most one selective nucleotide at its 3' end, preferably no selective nucleotides at is 3' end, i.e. the primer is only complementary to the adaptor (a +0 primer).

In alternative embodiments directed to the sequencing methods described herein, the primers used in the amplification may contain specific sections (as alternative to the herein described primer or primer binding sequences) that are used in the subsequent sequencing step to bind the adaptor-capped restriction fragments or amplicons to the surface. These are generally depicted as the key region or the 5'-primer compatible sequence.

Further Embodiments

In one aspect the invention is directed to a method for the detection of a mutation in a target sequence in a member of a mutagenized population comprising the steps of:

(a) Isolating genomic DNA of each member of the mutagenized population to provide for DNA samples of each member in the population;

(b) pooling the DNA obtained in step (a);

(c) amplifying the target sequence with a pair of (optionally labeled) primers from the DNA pools;

(d) pooling the amplification products of step (c) to create a library of amplification products;

(e) optionally, fragmenting the amplification products in the library;

(f) determining the nucleotide sequence of the products and/or fragments using high throughput sequencing;

(g) identifying mutations by clustering (aligning) the sequences of the fragments;

(h) screening the identified mutations for a modified function of the target sequence;

(i) designing a primer directed to hybridize to the identified mutation;

(j) amplifying the library of step (d) with the primer of step (i) and one of the primers of step (c);

(k) identifying the member(s) carrying the mutation;

(l) optionally, confirming the mutation by amplifying the target sequence from the member(s) of step (k) using the primers of step (c) and determining the sequence of the amplified product.

The isolation of DNA is generally achieved using common methods in the art such as the collection of tissue from a member of the population, DNA extraction (for instance using the Q-Biogene fast DNA kit), quantification and normalization to obtain equal amounts of DNA per sample. As an example, the present invention is illustrated based on a TILLING population of 3072 plants and a gene of 1500 bp.

The pooling of the isolated DNA can for instance be achieved using a 3-dimensional pooling scheme (Vandenbussche et al., 2003, *The Plant Cell*, 15: 2680-93). The pooling is achieved preferably using equal amounts of DNA. The 3D-pooling scheme may comprise 15×15×14, resulting in 44 pools (15+15+14) containing 3072/14=219 or 3072/15=205 different DNA samples per pool. Other pooling schemes can be used.

The pooling step typically serves to identify the plant containing an observed mutation after one round of PCR screening. Pooling of the DNA further serves to normalize the DNAs prior to PCR amplification to provide for a more equal representation in the libraries for sequencing. The additional advantage of the pooling of the DNA is that not all sequences have to be determined separately, but that the pools allow for rapid identification of the sequences of interest, in particular when tagged libraries are used. This facilitates the screening of large or complex populations in particular.

The amplification of the target sequence with a pair of optionally labeled primers from the pools can be achieved by using a set of primers that have been designed to amplify the gene of interest. As stated, the primers may be labeled to visualize the amplification product of the gene of interest.

The amplification products are pooled, preferably in equal or normalized amounts to thereby create a library of amplification products. Exemplary, the complexity of the library will be 3072 plants×1500 by gene sequence=4.6 Mb sequence.

The amplification products in the library may be randomly fragmented prior to sequencing of the fragments in case the PCR product length exceeds the average length of the sequence traces. Fragmentation can be achieved by physical techniques, i.e., shearing, sonication or other random fragmentation methods. In step (f), at least part, but preferably the entire, nucleotides sequence of at least part of, but preferably of all the fragments contained in the libraries is determined. In certain embodiments, the fragmentation step is optional. For instance, when the read length of the sequencing technique and the PCR fragments length are about the same, there is no need for fragmentation. Also in the case of larger PCR products this may not be necessary if it is acceptable that only part of the PCR product is sequenced for instance in case of 1500 bp PCR product and read length of 400 (from each side) 700 bp remain unsequenced.

The sequencing may in principle be conducted by any means known in the art, such as the dideoxy chain termination method (Sanger sequencing), but this is less preferred given the large number of sequences that have to be determined. It is however preferred and more advantageous that the sequencing is performed using high-throughput sequencing methods, such as the methods disclosed in WO 03/004690, WO 03/054142, WO 2004/069849, WO 2004/070005, WO 2004/070007, and WO 2005/003375 (all in the name of 454 Life Sciences), by Seo et al. (2004) *Proc. Natl.*

*Acad. Sci. USA* 101:5488-93, and technologies of Helios, Solexa, US Genomics, etcetera, which are herein incorporated by reference. It is most preferred that sequencing is performed using the apparatus and/or method disclosed in WO 03/004690, WO 03/054142, WO 2004/069849, WO 2004/070005, WO 2004/070007, and WO 2005/003375 (all in the name of 454 Life Sciences), which are herein incorporated by reference. The technology described allows sequencing of 40 million bases in a single run and is 100 times faster and cheaper than competing technology. The sequencing technology roughly consists of 5 steps: 1) fragmentation of DNA and ligation of specific adaptor to create a library of single-stranded DNA (ssDNA); 2) annealing of ssDNA to beads, emulsification of the beads in water-in-oil microreactors and performing emulsion PCR to amplify the individual ssDNA molecules on beads; 3) selection of/enrichment for beads containing amplified ssDNA molecules on their surface 4) deposition of DNA carrying beads in a PicoTiterPlate®; and 5) simultaneous sequencing in at least 100,000 wells by generation of a pyrophosphate light signal. The method will be explained in more detail below.

In a preferred embodiment, the sequencing comprises the steps of:

(a) annealing adapted fragments to beads, with a single adapted fragment being annealed to each bead;

(b) emulsifying the beads in water-in-oil microreactors, each water-in-oil microreactor comprising a single bead;

(c) loading the beads in wells, each well comprising a single bead; and generating a pyrophosphate signal.

In the first step (a), sequencing adaptors are ligated to fragments within the library. The sequencing adaptor includes at least a "key" region for annealing to a bead, a sequencing primer region and a PCR primer region. Thus, adapted fragments are obtained.

In a second step, adapted fragments are annealed to beads, each bead annealing with a single adapted fragment. To the pool of adapted fragments, beads are added in excess as to ensure annealing of one single adapted fragment per bead for the majority of the beads (Poisson distribution).

In a next step, the beads are emulsified in water-in-oil microreactors, each water-in-oil microreactor comprising a single bead. PCR reagents are present in the water-in-oil microreactors allowing a PCR reaction to take place within the microreactors. Subsequently, the microreactors are broken, and the beads comprising DNA (DNA positive beads) are enriched.

In a following step, the beads are loaded in wells, each well comprising a single bead. The wells are preferably part of a PicoTiter™ Plate allowing for simultaneous sequencing of a large amount of fragments.

After addition of enzyme-carrying beads, the sequence of the fragments is determined using pyrosequencing. In successive steps, the PicoTiter™ Plate and the beads as well as the enzyme beads therein are subjected to different deoxyribonucleotides in the presence of conventional sequencing reagents, and upon incorporation of a deoxyribonucleotide a light signal is generated which is recorded. Incorporation of the correct nucleotide will generate a pyrosequencing signal which can be detected.

Pyrosequencing itself is known in the art and described in e.g., WO 03/004690, WO 03/054142, WO 2004/069849, WO 2004/070005, WO 2004/070007, and WO 2005/003375 (all in the name of 454 Life Sciences), which are herein incorporated by reference.

The mutations are identified by clustering of the sequenced fragments in the amplified library. Identification of the mutations is achieved by aligning the determined sequences of the fragments of the libraries. The majority of the sequences are wild-type (not mutated) but the induced mutations and occasional sequencing errors are also observed. As the amplification libraries are sequenced with multifold redundancy (typically about 4- to 5-fold redundant), multiple observations of the same sequence change is indicative of a mutation rather than a sequencing error. See FIG. 6.

The clustering provides alignments of the fragments in the amplified library. In this way for each PCR product in the library, a cluster is generated from sequenced fragments, i.e., a contig of the fragments, is build up from the alignment of the sequence of the various fragments obtained from the fragmenting in step (e).

Methods of alignment of sequences for comparison purposes are well known in the art. Various programs and alignment algorithms are described in: Smith and Waterman (1981) Adv. Appl. Math. 2:482; Needleman and Wunsch (1970) J. Mol. Biol. 48:443; Pearson and Lipman (1988) Proc. Natl. Acad. Sci. USA 85:2444; Higgins and Sharp (1988) Gene 73:237-244; Higgins and Sharp (1989) CABIOS 5:151-153; Corpet et al. (1988) Nucl. Acids Res. 16:10881-90; Huang et al. (1992) *Computer Appl. in the Biosci.* 8:155-65; and Pearson et al. (1994) *Meth. Mol. Biol.* 24:307-31, which are herein incorporated by reference. Altschul et al. (1994) *Nature Genet.* 6:119-29 (herein incorporated by reference) present a detailed consideration of sequence alignment methods and homology calculations.

The NCBI Basic Local Alignment Search Tool (BLAST) (Altschul et al., 1990) is available from several sources, including the National Center for Biological Information (NCBI, Bethesda, Md.) and on the Internet, for use in connection with the sequence analysis programs blastp, blastn, blastx, tblastn and tblastx.

In the analysis of mutagenized populations, after the mutations have been identified, the identified mutations are assessed for a modified function of the associated gene, for instance the introduction of a stop codon. This assessment is performed on the sequence itself, for example by six-frame translation. Once the interesting mutations have been identified, the mutations are further investigated to identify the associated member of the population.

For each mutation that has been classified as an interesting mutation, an allele specific primer is designed that targets the mutation of interest. Thus, the allele specific primer is then used in combination with one of the primers used in the amplification of the pooled DNA samples (either the reverse or the forward primer). One or both of the primers may be labeled. The set of primers is used to amplify the pools of DNA. The positive pools are identified and the mutant plant is identified. In the above-mentioned 3D pooling scheme, the allele specific PCR with the set of primers to screen the 3D pooled DNA sample plates results in the identification of 3 positive pools (one in each dimension), which specifies the library address of the mutant plant.

In certain embodiments, the allele-specific primers comprise alternative nucleotides such as Locked Nucleic Acids (LNA) or Peptide Nucleic Acids (PNA) to increase their specificity. Such nucleic acids are widely known in the art and are commercially available from a choice of suppliers.

Confirmation of the mutation is achieved by amplification of the target sequence from the identified mutant plant. This amplification is performed with the primers from step (c). The nucleotide sequence of the amplified product is determined and by comparison with the consensus sequence, the mutation is identified. The sequencing is preferably performed Sanger sequencing.

In one aspect the invention pertains to a method for the detection of a mutation in a target sequence in a member of a mutagenized population comprising the steps of:

(a) isolating genomic DNA of each member of the mutagenized population to provide DNA samples of each member in the population;

(b) pooling the DNA obtained in step (a);

(c) amplifying a part or segment of the target sequence with a pair of tagged (optionally labeled) primers from the DNA pools, preferably wherein at least one of the primers comprise a gene-specific section, a tag and a sequence primer binding site;

(d) pooling the amplification products of step (c) to create a library of amplification products;

(d) determining the nucleotide sequence of the amplification products using high throughput sequencing;

(f) identifying mutations by clustering (aligning) the sequences of the fragments;

(g) identifying the member(s) having the mutation using the tags;

(h) optionally, confirming the mutation by amplifying the target sequence from the member(s) of step (g) using the primers of step (c) and determining the sequence of the amplified product.

The isolation of genomic DNA of the members of the mutagenized population and the pooling of the isolated DNA can be carried out essentially as described above.

A part or segment of the target sequence is amplified using a pair of tagged primers that may be labeled. Preferably, for each pool of each dimension, a different primer is used. In the above illustration this means that 44 forward and 44 reverse primers are preferred. Preferably, each of the forward and reverse primers comprises (i) a sequence primer binding site that can be used in the following sequencing step, (ii) a tag that serves to link the primer (and the resulting amplification product) to the original member of the population, and (iii) a gene specific sequence that is capable of annealing to the target sequence of interest (i.e., the gene).

In a typical embodiment the primer has the following order:

5'-Sequence Primer Binding Site—Tag—Gene Specific PCR Primer Sequence-3'

The length of the sequence primer binding site and the gene specific PCR primer sequence are those that are conventional in common PCR use, i.e., independently from about 10 to about 30 bp with a preference for from 15 to 25 bp. Preferably the part or segment of the sequence that is amplified corresponds to a length that can be sequenced in one run using the high throughput sequencing technologies described below. In certain embodiments the part or segment has a length of between about 50 bp to about 500 bp, preferably from about 75 bp to about 300 bp and more preferably between about 90 bp and about 250 bp. As stated above, this length may vary with the sequencing technology employed including those yet to be developed.

By using primers (forward and/or reverse) containing a tag sequence that is unique for each of the primers representing all pool dimensions, the specific plant origin of each tag sequence is known as the sequence primer anneals upstream of the tag and as a consequence, the tag sequence is present in each amplification product. In certain embodiments, both forward and reverse primers are tagged. In other embodiments, only on of the forward or reverse primers is tagged. The choice between one or two tags depends on the circumstances and depends on the read length of the high throughput sequencing reaction and/or the necessity of independent validation. In the case of, e.g., a 100 bp PCR product that is sequenced unidirectionally, only one tag is needed. In the case of a 200 bp PCR product and a 100 bp read-length, double tagging is useful in combination with bi-directional sequencing as it improves efficiency 2-fold. It further provides the possibility of independent validation in the same step. When a 100 bp PCR product is sequenced bi-directionally with two tagged primers, all traces, regardless of orientation, will provide information about the mutation. Hence both primers provide "address information" about which plant contains which mutation.

The tag can be any number of nucleotides, but preferably contains 2, 3, 4 or 5 nucleotides. With 4 nucleotides permuted, 256 tags are possible, whereas 3 nucleotides permuted provide 64 different tags. In the illustration used, the tags preferably differ by >1 base, so preferred tags are 4 by in length. Amplification using these primers results in a library of tagged amplification products.

In certain embodiments, a system of tags can be used wherein the amplification process includes (1) a long PCR primer comprising (a) a 5'-constant section linked to (b) a degenerate tag section (NNNN) linked to (c) a gene specific section-3' and (2) a short PCR primer in subsequent amplifications that consists of (a) the 5'-contact section linked to (b) non-degenerate tag section-3' (i.e., a selection amongst NNNN).

The non-degenerate tag section can be unique for each sample, for example, ACTG for sample 1, AATC for sample 2, etc. The short primer anneals to a subset of the long primer. The constant section of the primer can be used as a sequence primer. See FIG. 8.

The library preferably comprises equal, amounts of PCR products from all amplified pools. In the illustrative example, the library contains 3072 plants×100 bp=307 kb sequence to be determined.

The PCR products in the library are subjected to a sequencing process as disclosed above. In particular, the PCR products are attached to beads using the sequence primer binding site that corresponds to the sequence linked to the bead. Thus the present embodiment does not require fragmentation and adapter ligation. Rather, in this embodiment, the adapters have been introduced earlier via the PCR primer design. This improves the reliability of the method. Following the annealing to the beads, sequencing is performed as described above, i.e., (1) emulsification of the beads in water-in-oil microreactors, (2) emulsion PCR to amplify the individual ssDNA molecules on beads; (3) selection of/enrichment for beads containing amplified ssDNA molecules on their surface, (4) transfer of the DNA carrying beads to a PicoTiterPlate®; and (5) simultaneous sequencing in 100,000 wells by a method that generates a pyrophosphate light signal. Typical output is about 200.000× 100-200 by sequences, representing a 66 fold coverage of all PCR products in the library.

Clustering and alignment is performed essentially as described above. The individual plant containing the mutation can be identified using the tags. In the examples, the combination of the 3 tags denotes the positive pools and the consequently the coordinates of the individual plant in the pools.

Confirmation of the mutation by re-sequencing of the PCR product of the identified mutant sample is as described above.

Various pooling strategies can be used with the present invention, examples of which are multidimensional pooling (including 3D pooling) or column-, row- or plate pooling.

High throughput sequencing methods that can be used here are described, for example, in Shendure et al., *Science* 309:1728-32. Examples include microelectrophoretic sequencing, hybridization sequencing/sequencing by hybridization (SBH), cyclic-array sequencing on amplified molecules, cyclic-array sequencing on single molecules, non-cyclical, single-molecule, real-time methods, such as, polymerase sequencing, exonuclease sequencing, or nanopore sequencing.

For optimal results, fragments or amplified products should be sequenced with sufficient redundancy. Redundancy permits distinction between a sequencing error and a genuine possible mutation. In certain embodiments, the redundancy of the sequencing is preferable at least 4, more preferably at least 5, but, as can be seen from the Examples, redundancies of more than 10, preferably more than 25 or even more than 50 are considered advantageous, although not essential for this invention.

Advantages of the methods of the present invention reside inter alia in the fact that mutations can be assessed in silico for their impact on gene function, meaning that a selection is made for the active mutations. Mutations conferring only silent substitutions can be selected against, thereby making the overall process more economical and efficient. This is a particular advantage with regard to the known CEL I based TILLING technology because the majority of CEL I mutations are C/G to T/A transitions, of which only 5% commonly create stop codons (Colbert et al. 2001). The vast majority are missense mutations of reduced interest. Efficient recognition of members in a population with stop codon mutations economizes the process and obviates the need for additional screening of individual members of positive pools.

All mutations can be found with equal probability, irrespective of their position in the PCR product, in particular when the whole target sequence is screened.

The method further avoids the use of CEL I digestion, heteroduplex formation and cumbersome gel scoring. The invention is therefore insensitive to pooling limitations associated with CEL I technology.

The invention further relates to kits that may contain one or more compounds selected form the group consisting of: one or more (labeled) primers for a particular gene or trait, mutation- or allele-specific primers. The kits may further contain beads, sequencing primers, software, descriptions for pooling strategies and other components that are known for kits per se. In certain embodiments, kits are provided that are dedicated to find specific mutations, for instance disease-related mutations.

The present invention further embodies itself in adaptors containing pool-specific or degenerated identifier sections and/or in primers containing pool-specific identifiers, respectively.

WORKING EXAMPLES

Example 1

De Novo BAC-Based Physical Map Construction of *Arabidopsis thaliana* Based on a Sequencing by Synthesis (SBS) Approach This example is based on the following generalisations.

The total *Arabidopsis thaliana* genome is ~125 Mbp. A Bacterial Artificial Chromosome (BAC) has a genomic insert of ~100 kb on average. One Genome Equivalent (GE) of BACs for a 1× physical coverage of the *Arabidopsis* genome comprises ~1250 BACs. For optimal results, it is preferred that the construction of the BAC pools is such that one BAC pool contains not more than 0.34 GE (~384 BACs). Statistical analysis predicts that in 0.34 GE the chance of finding 2 identical BACs (that is 2 BACs that would map to the exact same physical position) is <5%. Lower GE' in a BAC pool further reduces the chance of finding two BACs mapping to the same position. A straightforward 3D-pooling system is used for the calculations. A total of 10 GE of BACs of 2 different high quality BAC libraries (2 different cloning enzymes eg. EcoRI and HindIII) are sufficient for the construction of a high quality physical map. 10 GE BACs for *Arabidopsis* is ~12.500 BACs.

The sequence Tags (the combination of part of the restriction fragment and identifier) are generated from a rare cutter restriction site, for example AFLP fragments such as EcoRI/MseI, or HindIII/MseI or a combination of several enzyme combinations (ECs).

In this example the enzyme combination HindIII/MseI is used. The distribution of HindIII/MseI fragments in the *Arabidopsis* genome is estimated to be between 50 to 120 fragments per 100 kb.

Set up for high throughput sequencing:

See also FIG. 1. 0.3 GE corresponds to 384 BACs. 3D-pooling of 384 BACs, with dimensions X+Y+Z results in 8+12+4=24 subpools. For 10 GE: M (X+Y+Z)=30 (8+12+4)=720 subpools.

For each subpool, the aim is to generate:
100 sequenced Tags per BAC
10 fold sequence redundancy per Tag
3 dimensional pooling (each BAC fragment is sequenced in each (X,Y,Z) dimension)

This means that for bridging amplification-based high throughput sequencing of a pool of 0.34GE, a set of sequencing reads of: 8 subpools×(12×4×100×10)+12 subpools×(8×4×100×10)+4 subpools×(12×8×100×10)= 1.152.000 reads are needed. This means for one GE that 3*1.152.000=3.456.000 reads per GE are needed and 10×3.456.000 reads per 10 GE=34.560.000 reads.

A single BAC generates a potential of ~100 unique sequence tags of ~20 bps (including the restriction site). The number of sequences will depend on the choice and/or combination of enzyme combinations.

The individual BAC coordinates and accompanying sequence tags can be deduced from the addressed subpool sequences by the "deconvolution" step. Consequently, via deconvolution each sequence tag is assignable to the corresponding individual BAC. Repetitive sequence tags are ignored. The deconvolution process will result in a string of 100 Tags per BACs, and subsequently the assembly of a de novo physical map is achieved through a FPC (FingerPrintedContigs) type process, as described by Cari Soderlund for BAC fragments analysed in agarose gels (Soderlund et al. 2000—Genome Research 10; 1772-1787). Finally, the anchoring of the physical map to the genetic map is performed in silico. For larger genomes other pooling strategies may be necessary.

De Novo BAC-Based Physical Map Construction of *Cucumis sativus* Based on a Sequencing by Synthesis (SBS) Approach This example is based on the following generalisations.

The total *Cucumis sativus* genome is ~350 Mbp. A Bacterial Artificial Chromosome (BAC) has a genomic insert of ~100 kb on average. One Genome Equivalent (GE) of BACs for a 1× physical coverage of the *Arabidopsis* genome comprises ~3500 BACs. For optimal results, it is preferred that the construction of the BAC pools is such that one BAC pool contains not more than 0.34 GE (~384 BACs). Statistical analysis predicts that in 0.34 GE the chance of finding 2 identical BACs (that is 2 BACs that would map to the exact same physical position) is <5%. Lower GE' in a BAC pool further reduces the chance of finding two BACs mapping to the same position. A straightforward 3D-pooling system is used for the calculations. A total of 10 GE of BACs of 2 different high quality BAC libraries (2 different cloning enzymes eg. EcoRI and HindIII) are sufficient for the construction of a high quality physical map. 10 GE BACs for *Cucumis* is ~35.000 BACs.

The sequence Tags (the combination of part of the restriction fragment and identifier) are generated from a rare cutter restriction site, for example AFLP fragments such as EcoRI/MseI, or HindIII/MseI or a combination of several enzyme combinations (ECs).

In this example the enzyme combination HindIII/MseI is used. The distribution of HindIII/MseI fragments in the *Cucumis sativus* genome is estimated to be between 50 to 120 fragments per 100 kb.

Set up for high throughput sequencing:

See also FIG. 1. 0.3 GE corresponds to 1152 BACs. 3D-pooling of 1152 BACs, with dimensions X+Y+Z results in 8+12+12=32 subpools. For 10 GE: M (X+Y+Z)=30 (8+12+12)=960 subpools.

For each subpool, the aim is to generate:
100 sequenced Tags per BAC
10 fold sequence redundancy per Tag
3 dimensional pooling (each BAC fragment is sequenced in each (X,Y,Z) dimension)

This means that for bridging amplification-based high throughput sequencing of a pool of 0.34GE, a set of sequencing reads of: 8 subpools×(12×12×100×10)+12 subpools×(8×12×100×10)+12 subpools×(12×8×100×10)= 3.456.000 reads are needed. This means for one GE that 3*3.456.000=10.368.000 reads per GE are needed and 10×10.368.000 reads per 10 GE=103.680.000 reads.

A single BAC generates a potential of ~100 unique sequence tags of ~20 bps (including the restriction site). The number of sequences will depend on the choice and/or combination of enzyme combinations.

The individual BAC coordinates and accompanying sequence tags can be deduced from the addressed subpool sequences by the "deconvolution" step. Consequently, via deconvolution each sequence tag is assignable to the corresponding individual BAC. Repetitive sequence tags are ignored. The deconvolution process will result in a string of 100 Tags per BACs, and subsequently the assembly of a de novo physical map is achieved through a FPC (FingerPrintedContigs) type process, as described by Cari Soderlund for BAC fragments analysed in agarose gels (Soderlund et al. 2000—Genome Research 10; 1772-1787). Finally, the anchoring of the physical map to the genetic map is performed in silico. For larger genomes other pooling strategies may be necessary.

AFLP templates (EcoRI/MseI or HindIII/MseI) are prepared from pooled BACs. AFLP amplification is performed using a combination 2 HindIII+1 primers and an MseI+0 primer (same for EcoRI). The use of two +1 primer ensures amplification of approximately 50% of the H/M (or E/M) fragments from the pools, i.e. on average 70/2=35 restriction fragments are amplified for each enzyme combination. The AFLP amplification reactions are performed with AFLP primers containing unique identifier tags at the 5'end for each of the BAC pools. Hence at least 74 identifier sequences are needed. This can be accomplished with 4 base tags ($4^4$=256 possibilities). Identifier sequences are only needed for the HindIII primer, since unidirectional sequencing will be performed in this example.

AFLP reaction mixtures of all pools are mixed in equal amounts, creating a fragment library. The fragment library is used to construct a sequence library.

Given a 3-D pooling strategy, this means that every fragment is sampled a plurality of times on average in each dimension. Results are 100 bp sequences derived from the HindIII (or EcoRI) site of the restriction fragments. As said, per BAC clone an average of 35 sequences are obtained. The sequences form the basis for contig assembly using a procedure similar to FPC (Software package by Soderlund obtainable from http://www.agcol.arizona.edu/software/fpc/) but based on sequence matching (more detailed).

The advantage of the use of reproducible complexity reduction is that less fragments are needed for the construction of a physical map. A complexity reduction of 50% in the above *Cucumis* example leads to 51.840.000 reads instead of 103.680.000. A further advantage of the present invention is, using complexity reduction as described herein, that physical maps can be generated of controllable quality. This means that by reducing a BAC pool in complexity by a +1 AFLP amplification, for instance a primer combination with +C, results in a physical map of about 25% of the quality (coverage) compared to a +1 amplification with all four primer combinations (A, C, T, G). However, when two or three primer combinations are used, increased coverage is obtained, i.e. for instance 55% or 90%, respectively, compared to the coverage obtained with a +1 amplification with all four primer combinations (A, C, T, G).

BAC clones addresses:

Fragments derived from the same BAC clone are amplified with 3 different tagged primers. Hence, unique sequences observed in combination with 3 tags are assigned to a single BAC clone in the library. Repeated sequences are observed in combinations with multiple tags and can therefore not be connected to a single BAC clone. This affects a considerable proportion of the fragments, but among 35 fragments/BAC clone, at a least a subset is unique.

A 10-fold sequence coverage of the BAC pools (3.3 fold/dimension) means that not all expected fragments are observed (due to concentration differences of individual clones and sampling variation etc). Hence a fraction of the (unique) sequences is only observed in combination with 1 or 2 tags (or not at all), which precludes assigning them to a single BAC clone. However, to the extent that this is due to sampling variation between the restriction fragments derived from the same clone, the fact that 35 fragments are sampled means that the combination of tags provides the correct address for the BAC: see below.

|  | Tag 1 | Tag 2 | Tag 3 |
|---|---|---|---|
| Fragment 1 | X | X |  |
| Fragment 2 |  | X | X |
| Fragment 3 |  | X | X |
| Fragment 4 | X |  | X |
| Fragment 5 | X | X | X |
| Etc. |  |  |  |
| Fragment 35 | X | X |  |

The scheme above illustrates that contig building groups the fragments together in a contig; fragment 5, which has a unique sequence and was sampled in combination with 3 tags defines the address of the BAC in library, from which fragment 1-4 (+35) are probably derived as well.

Hence, the strength of the approach is that sequence information on a sufficiently large number of restriction fragments (35 in the above example) is used to build accurate contigs, while the use of a 3 dimensional tagging system allow direct identification for the majority of BACs, even though the BAC address can not be derived from each individual fragment sequence (due to experimental variation). However, the combination of tags from fragments derived from the same BAC will provide the BAC address.

Thus, the information derived from sequence-based BAC contiging is the same as for conventional approaches (i.e. contig+BAC address). It is observed that for individual clone fingerprinting approaches, the BAC address will be known by definition.

Example 2

Procedure for High Throughput Physical Mapping by Sequence Tag BAC Mapping.

A total of 72 BACs (BAC=Bacterial Artificial Chromosome) mapping to chromosome 4 of *Arabidopsis* and spanning a total physical stretch of 5.4 Mb in 4 BAC contigs (1.8 Mb, 1.2 Mb, 0.5 Mb and 1.9 Mb) were selected from the TAIR and other databases. The donor plant of the BAC libraries is *Arabidopsis thaliana* ecotype Colombia. The 72 BACs, ranging in size between 70 kb and 150 kb, were separated in 2 groups of 36 BACs, group "AB" and group "XY". Within the 2 groups the 36 BACs have no internal overlap, while the BACs of group AB and group XY combined can be assembled into 4 continuous minimal tiling path contigs with alternating BACs from group AB and XY (see FIGS. 2-5).

Pooling Strategy for 72 *Arabidopsis* BACs, 36 in Group AB and 36 in Group XY

| GroupAB | | | | | |
| --- | --- | --- | --- | --- | --- |
| B1 | B2 | B3 | B4 | B5 | B6 |
| A1 F23J03 | T30A10 | T25P22 | T09A04 | T05L19 | F07L13 |
| A2 T12H20 | T22B04 | F25E04 | T26M18 | T04C09 | F07K02 |
| A3 F07K19 | F16G20 | T32A16 | T22A06 | F06i07 | F24A06 |
| A4 F08F16 | F28M20 | F10N07 | F08B04 | T16i18 | F04i10 |
| A5 T16L01 | F17i05 | F28A23 | T04L20 | T12J05 | F23E12 |
| A6 F14H08 | T19P05 | T10C14 | F06D23 | T03E09 | T06O13 |

| GroupXY | | | | | |
| --- | --- | --- | --- | --- | --- |
| Y1 | Y2 | Y3 | Y4 | Y5 | Y6 |
| X1 T03H13 | T08A17 | T15G18 | F17A08 | F28M11 | F24G24 |
| X2 T04F09 | F25i24 | F08L21 | T05C23 | F16J13 | T01P17 |
| X3 T12H17 | F21P08 | F09D16 | T19F09 | F22K18 | F13M23 |
| X4 T30C03 | F03L17 | F11C18 | F10M06 | F04D11 | F26P21 |
| X5 F17M05 | T09O24 | T04G07 | F10M10 | F11i11 | T04K12 |
| X6 F05M05 | T19K04 | F23E13 | T02G10 | F07O06 | T08H13 |

T = TAMU BAC library - 12.5 microgram chloramphenicol/ml
F = IGF BAC library - 50 microgram kanamycine/ml The 72 BACs were grown overnight as individual clones in 200 microliter standard TY medium including chloramphenicol (TAMU BAC clones) or kanamycine (IGF BAC clones). All clones were grown in a 6×6 format to facilitate the pooling procedure. In the morning the liquid culture was pooled in 2 dimensions (6×6) such that 12 pools per group were generated. Each pool contained 600 microliter of medium with grown BACs (100 microliter per individual BAC). DNA was isolated from all 24 BAC pools following a standard alkaline miniprep procedure according to Sambrook et al. (2001).

50 ng DNA of each BAC pool was digested with restriction enzymes EcoRI and MseI, and subsequently EcoRI and MseI AFLP adaptors were ligated, according to the standard AFLP procedure described by Vos et al. (1995). The restriction/ligation mix was diluted 10× in MilliQ-water and 5 microliter was used in the amplification step. The primers used in the amplification step were designed with a 4 nucleotide recognition sequence, such that each pool is tagged with a pool specific 4 nucleotide address-sequence. This recognition sequence is necessary to facilitate the deconvolution of all sequences to an individual BAC-coordinate.

Figure 4:
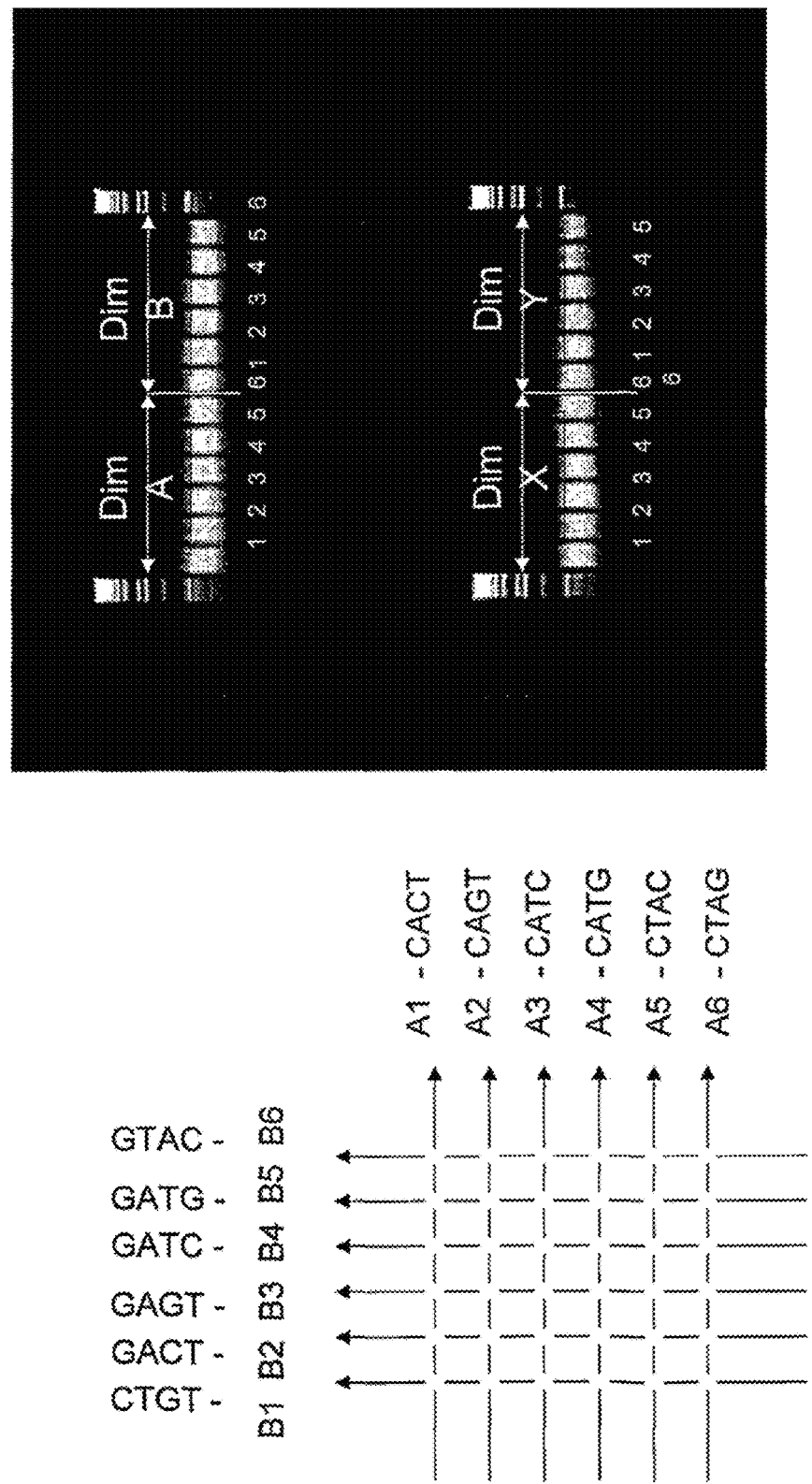
FIG. 4: recognition sequence addressed BAC pools— amplified product on agarose-gel
Figure 5:
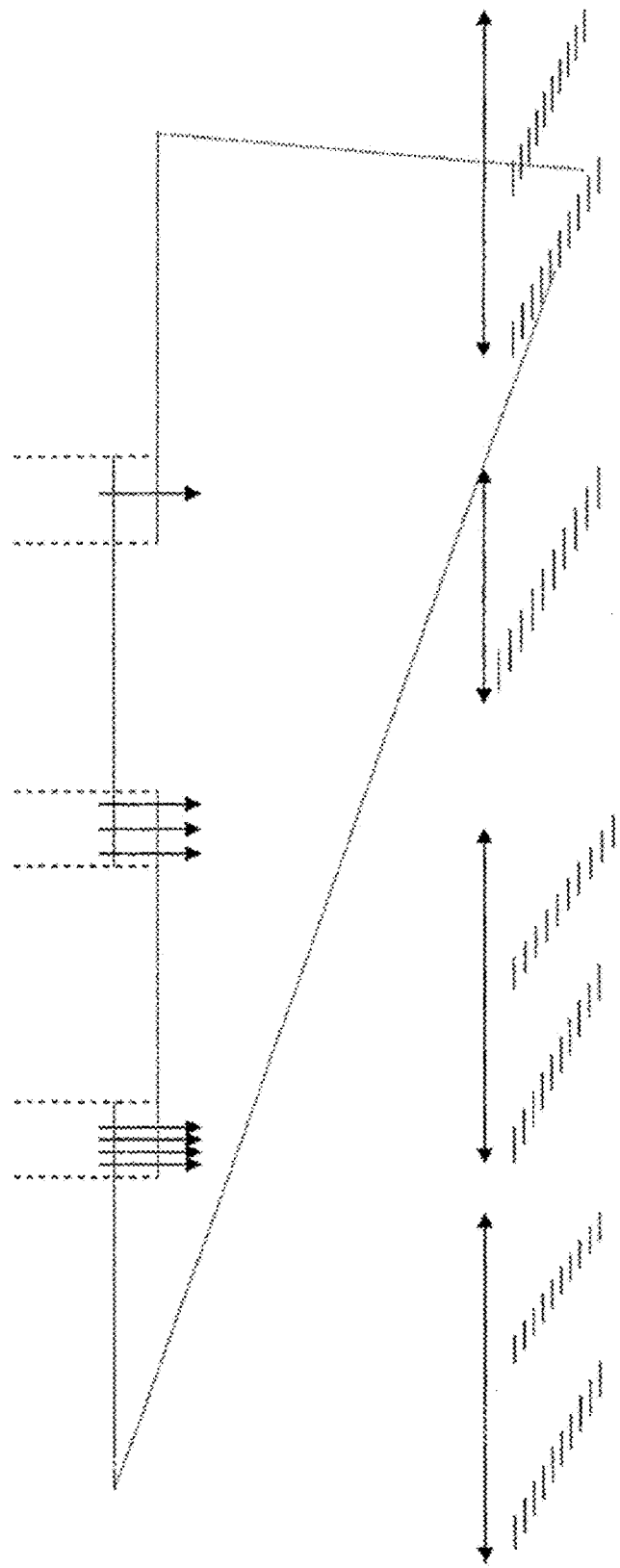
FIG. 5: Re-assembled minimal tiling path—part of the 1.9 Mb contig enlarged

Both the EcoRI+0 and MseI+0 primers used were adapter compatible 5'-phosphorylated primers carrying 5'-recognition sequences and are different for each pool coordinate (see FIG. 4). The 5'-phosphorylation is necessary for the ligation of the pyrosequencing adaptors. Amplification was performed for 30 cycles with the profile: 94° C. (30 sec), 56° C. (60 sec), 72° C. (60 sec). After amplification the products were checked on agarose gel (FIG. 4) and the 12 amplified pool-products of each group were pooled into a group-pool (AB cq. XY) and quantified. Five micrograms DNA of each group-pool was immediately processed in the further preparation steps for 454 sequencing. 454 pyrosequencing was performed on the GS20 platform according to Margulies et al. (2005).

Analysis of the Dataset and Assembly of the BAC Contigs

The list of DNA sequence reads as generated by the GS20 pyrosequencing machine were parsed in 3 steps:

Step 1) the first 4 nucleotides consisting of the pool sample code were identified and the corresponding pool-labels were assigned. If the code was unknown, the read was removed from the set.

Step 2) the next 16 or 17 nucleotides (depending on the restriction enzyme) containing the primer sequence were identified. When 100% identical to the primer sequence the reads were approved and added to the dataset and otherwise removed.

Step 3) all reads from step 2 were trimmed to 14 nucleotides after the primer sequence.

All correct trimmed sequence reads were subsequently grouped: all 100% identical reads were identified and assigned to their corresponding pool. Each unique group of reads is termed a 'tag'. Tags that were found in exactly 2 pools, both one for the X-coordinate and one for the Y-coordinate, were linked to a specific BAC: this procedure is called deconvolution.

All unique tags for deconvolved BACs were listed for both BAC groups. Pairs of BACs with one or more common tags were identified. Subsequently the BAC contigs could be assembled as shown in table 1.

TABLE 1

BAC links from all sequence tags, common between pairs of BACs (e.g. X1Y1 and A1B1) and occurring at least 2 times in each pool. Contigs are numbered.

| BAC link | NrTags | Contig |
| --- | --- | --- |
| X1Y1_A1B1 | 8 | Contig1 |
| X1Y2_A1B1 | 18 | Contig1 |
| X1Y2_A1B2 | 6 | Contig1 |
| X1Y3_A1B2 | 19 | Contig1 |
| X1Y3_A1B3 | 3 | Contig1 |
| X1Y4_A1B3 | 10 | Contig1 |
| X1Y4_A1B5 | 10 | Contig1 |
| X1Y5_A1B4 | 16 | Contig1 |
| X1Y5_A1B5 | 12 | Contig1 |

TABLE 1-continued

BAC links from all sequence tags, common between pairs of BACs (e.g. X1Y1 and A1B1) and occurring at least 2 times in each pool. Contigs are numbered.

| BAC link | NrTags | Contig |
|---|---|---|
| X1Y6__A1B4 | 13 | Contig1 |
| X1Y6__A1B6 | 4 | Contig1 |
| X2Y1__A1B6 | 1 | Contig1 |
| X2Y1__A2B1 | 3 | Contig1 |
| X2Y2__A2B1 | 4 | Contig1 |
| X2Y2__A2B2 | 2 | Contig1 |
| X2Y3__A2B2 | 5 | Contig1 |
| X2Y4__A2B3 | 4 | Contig2 |
| X2Y4__A2B4 | 2 | Contig2 |
| X2Y5__A2B4 | 1 | Contig2 |
| X2Y5__A2B5 | 1 | Contig2 |
| X2Y6__A2B5 | 4 | Contig2 |
| X3Y1__A2B6 | 3 | Contig3 |
| X3Y1__A3B1 | 5 | Contig3 |
| X3Y2__A3B1 | 4 | Contig3 |
| X3Y2__A3B2 | 2 | Contig3 |
| X3Y3__A3B2 | 1 | Contig3 |
| X3Y3__A3B3 | 5 | Contig3 |
| X3Y4__A3B3 | 15 | Contig3 |
| X3Y4__A3B4 | 1 | Contig3 |
| X3Y5__A3B4 | 2 | Contig3 |
| X3Y5__A3B5 | 13 | Contig3 |
| X3Y6__A3B5 | 7 | Contig3 |
| X3Y6__A3B6 | 7 | Contig3 |
| X4Y1__A3B6 | 10 | Contig3 |
| X4Y2__A4B1 | 12 | Contig4 |
| X4Y2__A4B2 | 4 | Contig4 |
| X4Y3__A4B2 | 5 | Contig4 |
| X4Y3__A4B3 | 20 | Contig4 |
| X4Y4__A4B3 | 5 | Contig4 |
| X4Y4__A4B4 | 11 | Contig4 |
| X4Y5__A4B5 | 9 | Contig5 |
| X4Y6__A4B5 | 7 | Contig5 |
| X4Y6__A4B6 | 6 | Contig5 |
| X5Y1__A5B1 | 6 | Contig6 |
| X5Y2__A5B1 | 5 | Contig6 |
| X5Y2__A5B2 | 28 | Contig6 |
| X5Y3__A5B2 | 4 | Contig6 |
| X5Y3__A5B3 | 26 | Contig6 |
| X5Y4__A5B4 | 4 | Contig7 |
| X5Y5__A5B4 | 3 | Contig7 |
| X5Y5__A5B5 | 1 | Contig7 |
| X5Y6__A5B5 | 16 | Contig7 |
| X5Y6__A5B6 | 19 | Contig7 |
| X6Y1__A5B6 | 7 | Contig7 |
| X6Y1__A6B1 | 14 | Contig7 |
| X6Y2__A6B1 | 3 | Contig7 |
| X6Y2__A6B2 | 14 | Contig7 |
| X6Y3__A6B2 | 14 | Contig7 |
| X6Y3__A6B3 | 8 | Contig7 |
| X6Y4__A6B3 | 14 | Contig7 |
| X6Y5__A6B5 | 13 | Contig8 |
| X6Y6__A6B5 | 8 | Contig8 |
| X6Y6__A6B6 | 14 | Contig8 |

It was demonstrated that the 4 BAC minimal tiling paths of 1.8 Mb, 1.2 Mb, 0.5 Mb and 1.9 Mb could be reassembled in a straightforward way after the deconvolution of sequence tags to the individual BACs (table 1 and FIG. 4). A comparison of the generated GS20 tags with predicted fragments in silico showed that 70 to 80% of the EcoRI/MseI fragments were sequenced. Therefore in the reassembly of the 4 BAC contigs some of the smaller physical overlaps between 2 BACs could not be detected.

The fact that short reads (14 bp) are sufficient to reassemble the BAC tiling paths indicates that high throughput sequencing platforms with short read length (such as the Illumina Genome Analyser and SOliD (ABI)) enables high throughput physical map assembly following the proposed method.

Example 3

Screening a TILLING Population can be Advanced by Using Novel High-Throughput sequencing methods, such as that of 454 Life Sciences (Margulies et al., 2005) or Polony Sequencing (Shendure et al., 2005). With the current state-of-the-art, 454 Life Sciences technology produces approximately 20 Mb sequence in a single sequencing run. Read lengths are approximately 100 bp per read. Assuming the screening of a population consisting of 3072 plants for mutations in a 1500 bp gene (as described in the above-cited reference in Chapter 2), two approaches are envisaged and described in more detail below.

(1) an approach where the entire 1500 bp gene is investigated for the presence of EMS induced mutations; and (1) an approach where one or several 100 bp stretches are investigated for the presence of EMS-induced mutations.

Screening the Entire 1500 by Region:

Genomic DNA of 3072 plants of the TILLING population is isolated. A 3-D pooling scheme of equal amounts of DNA per plant is set up (e.g., 15×15×14), resulting in 44 pools (15+15+14=44) containing 3072/14=219 or 3072/15=205 different DNA samples (Vandenbussche et al., supra).

This pooling step serves to permit identification of a plant containing an observed mutation after one round of PCR screening (step 8). Pooling of genomic DNAs further serves to normalize DNAs prior to PCR amplification to increase the probability that all DNAs are represented equally in the sequence library.

The 1500 bp gene is amplified from the pooled DNA samples using 1 pair of unlabelled PCR primers.

Equal amounts of PCR products from all pools wells are pooled to create a pooled PCR products library (complexity 3072 plants×1500 bp=4.6 Mb sequence).

The pooled PCR product library is subjected to shotgun sequencing using conventional technologies (such as those provided by 454 Life Sciences) wherein PCR products are randomly fragmented, amplified on individual beads and sequenced on the bead. Output is approximately 200,000 100 bp sequences, representing 4- to 5-fold coverage of all PCR products in the library).

Figure 6:
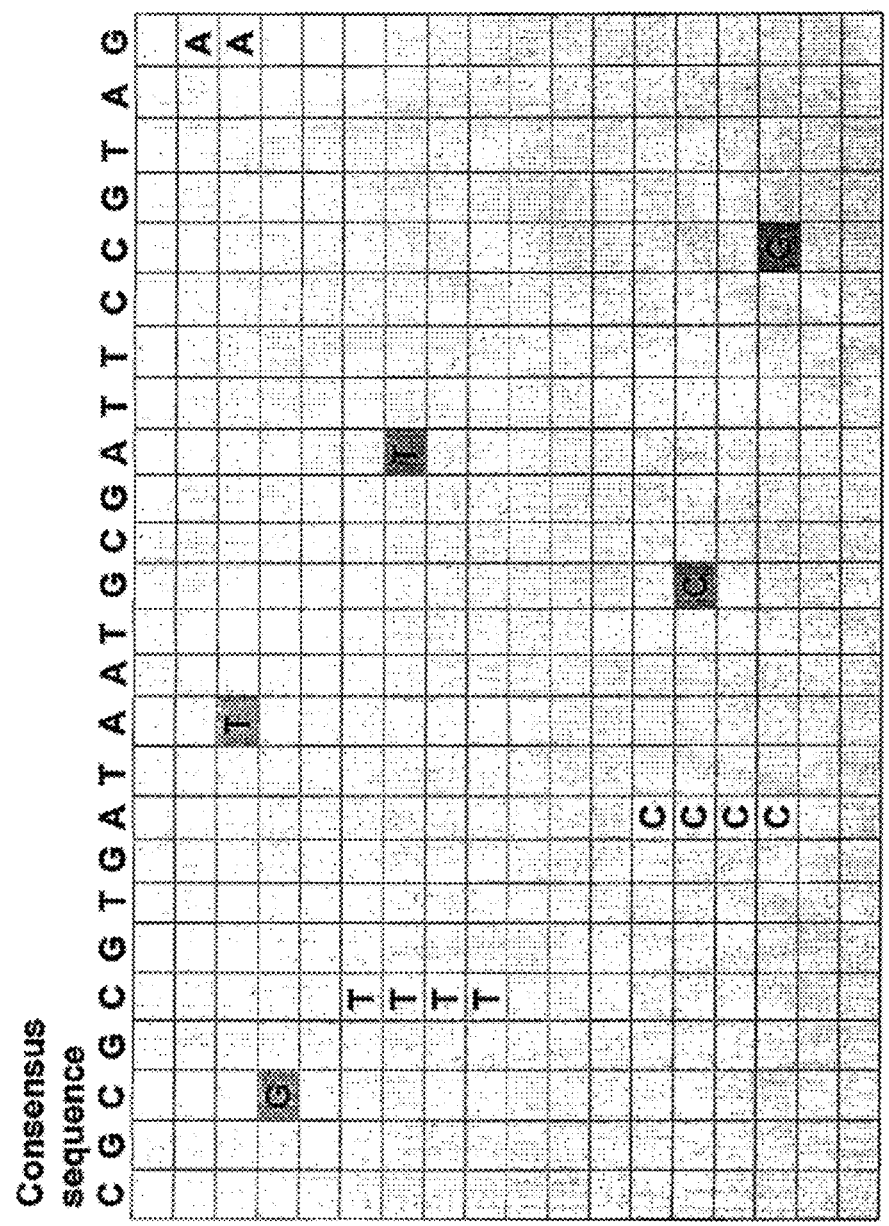
FIG. 6: Schematic representation of clustered sequences resulting from shotgun sequencing a gene to identify EMS-induced mutations. Mutations are lighter, sequence errors darker colored. Sequence errors are expected to be observed randomly and most often just once.

All sequences are clustered. The majority of sequences are wild-type but EMS-induced mutations (and sequence errors) are observed as well. Since PCR products are sequenced with 4-5 fold redundancy, multiple observations of the same sequence change is indicative of a mutation rather than a sequencing error (FIG. 6).

Mutations are assessed for their impact on gene function such as introduction of a stop-codon.

An allele-specific primer targeting a mutation of interest (with 3' Locked Nucleic Acid; LNA; or Peptide Nucleic Acid; PNA) is designed to be used in combination with either the forward or reverse primer used in step 3 to screen the 3-D pooled DNA sample plate. Allele-specific PCR will result in three positive pools (one of each dimension), which specifies the library address of the mutant plant.

The mutation is confirmed by amplifying the 1500 bp gene using the primers of step 3, followed by (bi-directional) Sanger sequencing.

Screening 100 bp Stretches (100 by is the read length of one 454 sequence run)

Genomic DNA of 3072 plants of the TILLING population is isolated. A 3-D pooling scheme of equal amounts of DNA per plant is set up (e.g., 15×15×14), resulting in 44 pools (15+15+14=44) containing 3072/14=219 or 3072/15=205 different DNA samples (Vandenbussche et al., supra).

This pooling step serves to permit identification of the plant containing an observed mutation directly from the sequence data. Pooling of genomic DNAs further serves to normalize DNAs prior to PCR amplification to increase the probability that all DNAs are represented equally in the sequence library.

A 100 bp (or 200 bp) region of the gene is amplified from a the pools by PCR using tagged unlabelled PCR primers. This requires 44 forward and 44 reverse primers (one for each pool of each dimension) with the following configuration:

5'-Sequence Primer Binding Site—4 bp Tag—Gene Specific Primer Sequence-3'.

By using tailed forward and reverse primers containing a 4 bp sequence tag that is different for each of the 44 primers representing all pool dimensions, the specific plant origin of each sequence is known as the sequence primer anneals upstream of the tag. Hence the tag sequence in present in each sequence trace. A 4 bp tag allows $4^4=256$ different tags. A 3 bp tag allows 64 different tag sequences—sufficient to distinguish 44 tags—but tag sequences differing by more than 1 base are preferred.

Equal amounts of PCR products from all pools wells are pooled to create a pooled PCR products library (complexity 3072 plants×100 bp=307 kb sequence).

The pooled PCR product library is provided to 454 for sequencing, i.e., PCR products are amplified and sequenced on the beads. Output is approximately 200,000 100 bp sequences, representing 66-fold coverage of all PCR products in the library.

All sequences (from either direction) are clustered; the majority of sequences are wild-type sequences but EMS-induced mutations (and sequence errors) are observed as well. Since PCR products are sequenced with 66 fold redundancy, multiple observations of the same sequence change are indicative of a mutation rather than a sequencing error (FIG. 6).

Figure 7:
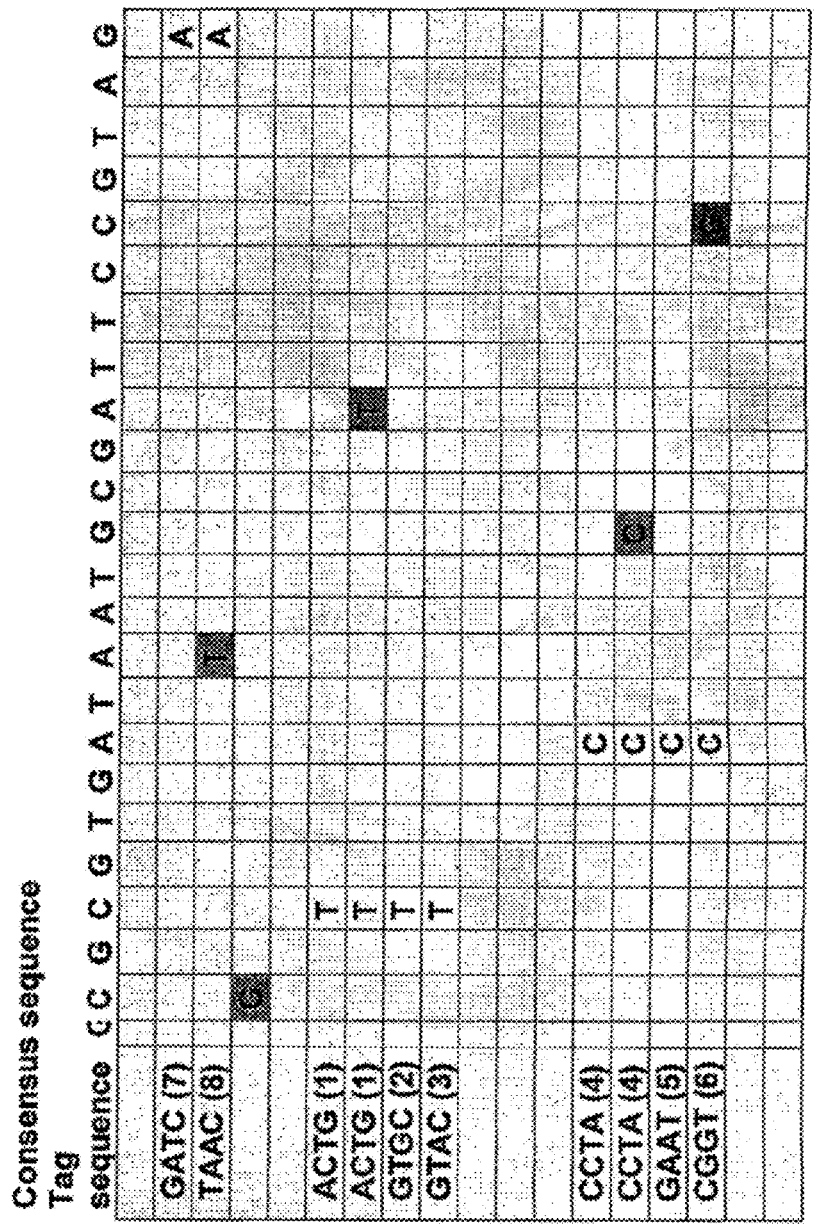
FIG. 7: Schematic representation of clustered tagged sequencing resulting from a 100 bp gene region amplified with 4 bp—tagged PCR primers from a 3-D pooled library.

The coordinates of the individual plant containing the mutation will be known immediately based on the unique combination of 3 tags sequences that occur in the sequence traces harboring the mutation (FIG. 7).

The mutation is confirmed by amplifying the 1500 bp gene using the primers of step 3, followed by (bi-directional) Sanger sequencing.

Example 4. Identifying Specific Mutations in a Mutant Library of Tomato

Mutant Library of Tomato

This example describes the screening of a mutant library of tomato by massive parallel sequencing in order to identify point mutations in a specific locus (target gene). The mutant library used is an isogenic library of inbred determinate tomato cultivar M82 consisting of 5075 M2 families derived from EMS mutagenesis treatments. Seeds of each of the 5075 M2 families were stored at 10% RH and 7° C. The origin and characteristics of the library are described in Menda et al. (*Plant J.* 38: 861-872, 2004).

DNA Isolation

Leaf material was harvested from 5 individual greenhouse-grown plants of each of 3072 M2 families randomly chosen from the library. As any mutation occurring in the library will segregate in a Mendelian fashion in the M2 offspring, the pooling of the leaf material of 5 individual M2 plants reduced the likelihood of overlooking any mutation as a consequence of segregation to less than 0.1%. Genomic DNA was isolated from the pooled leaf material using a modified CTAB procedure described by Stuart and Via (*Biotechniques*, 14: 748-750, 1993). DNA samples were diluted to a concentration of 100 ng/μl in TE (10 mM Tris-HCl pH 8.0, 1 mM EDTA) and stored at −20° C. in 96-well microtitre plates.

3D Pooling of the DNA Samples

The isolated DNA samples were normalized to a concentration of 20 ng/μl and subsequently pooled 4-fold resulting in 768 samples comprised in eight 96-well microtitre plates. Subsequently, these eight microtitre plates were subjected to a 3D pooling strategy, resulting in 28 pools of DNA. The 3D pooling strategy consisted of pooling together all DNAs in three different manners, thus ensuring that each single 4-fold pool occurs only once in an X-coordinate pool, only once in a Y-coordinate pool and only once in a Z-coordinate pool. X-pools were assembled by pooling all DNA samples together per column of eight wells (e.g. AH-11) from all eight microtitre plates, resulting in 12 X-pools. Each X-pool therefore held 8 (wells in a column)×8 (plates)=64 samples of 4-fold pools, representing 256 M2 families. Y-pools were assembled by pooling all DNA samples together per row of twelve wells (e.g. A1-A12) from all eight microtitre plates, resulting in 8 Y-pools. Each Y-pool therefore held 12 (wells in a row)×8 (plates)=96 samples of 4-fold pools, representing 384 M2 families. Z-pools were assembled by pooling all DNA samples together from an entire microtitre plate, resulting in 8 Z-pools. Each Z-pool therefore held 12×8=96 samples of 4-fold pools, representing 384 M2 families.

Target Locus

The target locus in this example was part of the tomato gene for eukaryotic initiation factor 4E (eIF4E). This gene has been shown to be involved in susceptibility to infection of potyviruses in *Arabidopsis* (Duprat et al., *Plant J.* 32: 927-934, 2002), lettuce (Nicaise et al. *Plant Physiol.* 132: 1272-1282, 2003) and Solanaceae (Ruffel et al., *Plant J.* 32: 1067-1075, 2002; *Mol. Gen. Genomics* 274: 346-353, 2005), and specific mutations in this gene are associated with recessive potyvirus resistance. The mutation screening described in this example was aimed to identify additional mutations in the tomato eIF4E gene as possible sources of new potyvirus resistance. For the tomato eIF4E, only the cDNA sequence was known (NCBI accession numbers AY723733 and AY723734). Using a PCR approach using primers designed on the basis of the cDNA sequence, fragments of the genomic sequence of the eIF4E locus of tomato cultivar Moneyberg were amplified and sequenced. This resulted in a sequence of most of the genomic locus of tomato eIF4E. The locus consists of 4 exons and 3 introns. For the mutation screening, exon 1 of the gene was chosen as the target sequence (SEQ ID NO: 57).

```
SEQ ID NO: 57: Sequence of exon 1 of tomato
Moneyberg eIF4E:
ATGGCAGCAGCTGAAATGGAGAGAACGATGTCGTTTGATGCAGCTGAGAA

GTTGAAGGCCGCCGATGGAGGAGGAGGAGAGGTAGACGATGAACTTGAAG

AAGGTGAAATTGTTGAAGAATCAAATGATACGGCATCGTATTTAGGGAAA

GAAATCACAGTGAAGCATCCATTGGAGCATTCATGGACTTTTTGGTTTGA

TAACCCTACCACTAAATCTCGACAAACTGCTTGGGGAAGCTCACTTCGAA

ATGTCTACACTTTCTCCACTGTTGAAAATTTTTGGGG
```

Primer Design for Target Locus Amplification

Primers were designed for the PCR amplification of exon 1 of tomato eIF4E. The forward primers were designed to correspond to the ATG start codon of the Open Reading Frame of exon 1, with 5' of the ATG a tag sequence of four bases, providing a unique identifier for each of the 28 pools. At the far 5' end of the forward PCR primers, a 5'-C was added. All primers were phosphorylated at their 5' end to facilitate subsequent ligation of adaptors. The sequence and names of the 28 forward primers are listed in Table 2. The tag sequences are underlined.

TABLE 2

Forward primers, sequences and pool identification for exon 1 amplification.

| name | sequence | 3D pool | SEQ ID NO: |
|---|---|---|---|
| 06I009 | CACACATGGCAGCAGCTGAAATGG | X1 | SEQ ID NO: 1 |
| 06I010 | CACAGATGGCAGCAGCTGAAATGG | X2 | SEQ ID NO: 2 |
| 06I011 | CACGAATGGCAGCAGCTGAAATGG | X3 | SEQ ID NO: 3 |
| 06I012 | CACGTATGGCAGCAGCTGAAATGG | X4 | SEQ ID NO: 4 |
| 06I013 | CACTCATGGCAGCAGCTGAAATGG | X5 | SEQ ID NO: 5 |
| 06I014 | CACTGATGGCAGCAGCTGAAATGG | X6 | SEQ ID NO: 6 |
| 06I015 | CAGACATGGCAGCAGCTGAAATGG | X7 | SEQ ID NO: 7 |
| 06I016 | CAGAGATGGCAGCAOCTGAAATGG | X8 | SEQ ID NO: 8 |
| 06I017 | CAGCAATGGCAGCAGCTGAAATGG | X9 | SEQ ID NO: 9 |
| 06I018 | CAGCTATGGCAGCAGCTGAAATGG | X10 | SEQ ID NO: 10 |
| 06I019 | CAGTCATGGCAGCAGCTGAAATGG | X11 | SEQ ID NO: 11 |
| 06I020 | CAGTGATGGCAGCAGCTGAAATGG | X12 | SEQ ID NO: 12 |
| 06I021 | CATCGATGCAGCAGCTGAAATGG | Y1 | SEQ ID NO: 13 |
| 06I022 | CATGCATGGCAGCAGCTGAAATGG | Y2 | SEQ ID NO: 14 |
| 06I023 | CTACGATGGCAGCAGCTGAAATGG | Y3 | SEQ ID NO: 15 |
| 06I024 | CTAGCATGGCAGCAGCTGAAATGG | Y4 | SEQ ID NO: 16 |
| 06I025 | CTCACATGGCAGCAGCTGAAATGG | Y5 | SEQ ID NO: 17 |
| 06I026 | CTCAGATGGCAGCAGCTGAAATGG | Y6 | SEQ ID NO: 18 |
| 06I027 | CTCGAATGGCAGCAGCTGAAATGG | Y7 | SEQ ID NO: 19 |
| 06I028 | CTCGTATGGCAGCAGCTGAAATGG | Y8 | SEQ ID NO: 20 |
| 06I029 | CTCTCATGGCAGCAGCTGAAATGG | Z1 | SEQ ID NO: 21 |
| 06I030 | CTCTGATGGCAGCAGCTGAAATGG | Z2 | SEQ ID NO: 22 |
| 06I031 | CTGACATGGCAGCAGCTGAAATGG | Z3 | SEQ ID NO: 23 |
| 06I032 | CTGAGATGGCAGCAGCTGAAATGG | Z4 | SEQ ID NO: 24 |
| 06I033 | CTGCAATGGCAGCAGCTGAAATGG | Z5 | SEQ ID NO: 25 |
| 06I034 | CTGCTATGGCAGCAGCTGAAATGG | Z6 | SEQ ID NO: 26 |
| 06I035 | CTGTCATGGCAGCAGCTGAAATGG | Z7 | SEQ ID NO: 27 |
| 06I036 | CTGTGATGGCAGCAGCTGAAATGG | Z8 | SEQ ID NO: 28 |

The reverse primers were designed to correspond to basepair position 267 to 287 of exon 1 in the non-coding strand. Again, 5' of the priming part the same series of tag sequences of four bases were included, providing a identifier for each of the 28 pools. At the far 5' end of the reverse PCR primers, a 5'-C was added. All primers were phosphorylated at their 5' end to facilitate subsequent ligation of adaptors. The sequence and names of the 28 reverse primers are listed in Table 3. The tags are underlined.

TABLE 3

Reverse primers sequences and pool identification for exon 1 amplification.

| name | sequence | 3D pool | SEQ ID NO: |
|---|---|---|---|
| 06I037 | CACACCCCCAAAAATTTTCAACAGTG | X1 | SEQ ID NO: 29 |
| 06I038 | CACAGCCCCAAAAATTTTCAACAGTG | X2 | SEQ ID NO: 30 |
| 06I039 | CACGACCCCAAAAATTTTCAACAGTG | X3 | SEQ ID NO: 31 |
| 06I040 | CACGTCCCCAAAAATTTTCAACAGTG | X4 | SEQ ID NO: 32 |
| 06I041 | CACTCCCCCAAAAATTTTCAACAGTG | X5 | SEQ ID NO: 33 |
| 06I042 | CACTGCCCCAAAAATTTTCAACAGTG | X6 | SEQ ID NO: 34 |
| 06I043 | CAGACCCCCAAAAATTTTCAACAGTG | X7 | SEQ ID NO: 35 |
| 06I044 | CAGAGCCCCAAAAATTTTCAACAGTG | X8 | SEQ ID NO: 36 |
| 06I045 | CAGCACCCCAAAAATTTTCAACAGTG | X9 | SEQ ID NO: 37 |
| 06I046 | CAGCTCCCCAAAAATTTTCAACAGTG | X10 | SEQ ID NO: 38 |
| 06I047 | CAGTCCCCCAAAAATTTTCAACAGTG | X11 | SEQ ID NO: 39 |
| 06I048 | CAGTGCCCCAAAAATTTTCAACAGTG | X12 | SEQ ID NO: 40 |
| 06I049 | CATCGCCCCAAAAATTTTCAACAGTG | Y1 | SEQ ID NO: 41 |
| 06I050 | CATGCCCCCAAAAATTTTCAACAGTG | Y2 | SEQ ID NO: 42 |
| 06I051 | CTACGCCCCAAAAATTTTCAACAGTG | Y3 | SEQ ID NO: 43 |
| 06I052 | CTAGCCCOCAAAAATTTTCAACAGTG | Y4 | SEQ ID NO: 44 |
| 06I053 | CTCACCCCCAAAAATTTTCAACAGTG | Y5 | SEQ ID NO: 45 |
| 06I054 | CTCAGCCCCAAAAATTTTCAACAGTG | Y6 | SEQ ID NO: 46 |
| 06I055 | CTCGACCCCAAAAATTTTCAACAGTG | Y7 | SEQ ID NO: 47 |
| 06I056 | CTCGTCCCCAAAAATTTTCAACAGTG | Y8 | SEQ ID NO: 48 |
| 06I057 | CTCTCCCCCAAAAATTTTCAACAGTG | Z1 | SEQ ID NO: 49 |
| 06I058 | CTCTGCCCCAAAAATTTTCAACAGTG | Z2 | SEQ ID NO: 50 |
| 06I059 | CTGACCCCCAAAAATTTTCAACAGTG | Z3 | SEQ ID NO: 51 |
| 06I060 | CTGAGCCCCAAAAATTTTCAACAGTG | Z4 | SEQ ID NO: 52 |
| 06I061 | CTGCACCCCAAAAATTTTCAACAGTG | Z5 | SEQ ID NO: 53 |
| 06I062 | CTGCTCCCCAAAAATTTTCAACAGTG | Z6 | SEQ ID NO: 54 |
| 06I063 | CTGTCCCCCAAAAATTTTCAACAGTG | Z7 | SEQ ID NO: 55 |
| 06I064 | CTGTGCCCCAAAAATTTTCAACAGTG | Z8 | SEQ ID NO: 56 |

Target Locus Amplification

The exon 1 of the target locus was amplified from the 3D pooled DNAs using the forward and reverse primers described above. For each PCR reaction, a forward and a reverse primer were used with identical tags. For the amplification of exon 1 from each of the 28 3D pools, a different set of forward and reverse primers was used.

The PCR amplification reaction conditions for each sample were as follows:

25 µl DNA (=50 ng); 5 µl RNase-mix; 10 µl 5× Herculase PCR-buffer; 0.6 µl of the four dNTPs (20 mM); 1.25 µl forward primer (50 ng/µl); 1.25 µl reverse primer (50 ng/μl); 0.5 μl Herculase DNA polymerase; 28.9 μl milliQ-purified water. The RNase-mix consisted of 157.5 milliQ-purified water+17.5 μl RNase.

PCR amplifications were performed in a PE9600 thermocycler with a gold or silver block using the following conditions: 2 minutes hot-start of 94° C., followed by 35 cycles of 30 sec at 94° C., 30 sec at 53° C., 1 min at 72° C., and a final stationary temperature of 4° C. The PCR amplification efficiency was checked by analysis of 10 μl of PCR products on a 1% agarose gel. FIG. 9 shows the efficient amplification of exon 1 PCR products from each of the 28 3D pools in comparison to a concentration range of lambda DNA on the same gel.

Following amplification, equal amounts of PCR products were mixed and purified using the QIAquick PCR Purification Kit (QIAGEN), according to the QIAquick® Spin handbook (page 18). On each column a maximum of 100 μl of product was loaded. Products were eluted in 10 mM Tris-EDTA.

Sequence Library Preparation and High-Throughput Sequencing

Mixed amplification products from the 3D pools were subjected to high-throughput sequencing on a GS20 sequencer using 454 Life Sciences sequencing technology as described by Margulies et al. (*Nature* 437: 376-380, 2005, and Online Supplements). Specifically, the PCR products were ligated to adaptors to facilitate emulsion-PCR amplification and subsequent fragment sequencing as described by Margulies et al. The 454 adaptor sequences, emulsion PCR primers, sequence primers and sequence run conditions were all as described by Margulies et al. The linear order of functional elements in an emulsion-PCR fragment amplified on Sepharose beads in the 454 sequencing process was as follows:

454 PCR adaptor—454 sequence adaptor—C-nucleotide—4 by tag—target amplification primer sequence 1—target fragment internal sequence—target amplification primer sequence 2-4 by tag—G-nucleotide—454 sequence adaptor—454 PCR adaptor—Sepharose bead.

454 Sequence Run Data-Processing.

After base calling with 454 software for each region of the microtiter plate a file with FASTA formatted sequences was produced. These were concatenated into one file. Within this file a search was conducted with a regular expression to a 100% match of the forward primer preceded with 5 nucleotides (C plus four by tag sequence). The same was done with the reverse primer extended with 5 nucleotides (C plus tag sequence). All sequences were then grouped by their tag sequence (pool indentifiers) in separate files. Each file was analysed with the ssahaSNP tool and the known exon 1 nucleotide sequence as a reference. The ssahaSNP tool reported about all single nucleotide sequence differences and "indels" (single base insertions or deletions as a result of either mutagenesis or erroneous base-calling) of the 454 sequences versus the reference genome. These single nucleotide sequence difference and indel statistics were saved in a database and used for error rate analysis and point mutation identification.

454 Sequencing Error Rate

The total number of correct sequences obtained from the data processing for all 28 pools combined was 247,052. The sequences were divided in two groups, those that aligned with the forward primer and coding strand (5' end) of the exon 1 PCR product (128,594=52%), and those that aligned with the reverse primer and the complementary strand of the PCR product (118,458=48%). The number of sequences obtained from each of the different pools and alignment groups ranged from 69 to 7269. On average, each of the 3072 M2 families should be represented 80 times in the total collection of sequences, and each allele 40 times.

Within the alignment group corresponding to the forward primer, 1338 sequences out of 128,594 (1.2%) showed one or more single nucleotide sequence differences in relation to the eIF4E reference sequence along a stretch of 63 bases of aligned target sequence. For the reverse primer group, 743 sequences out of 118,458 (0.6%) showed one or more single nucleotide sequence differences in relation to the eIF4E reference sequence along a stretch of 102 bases of aligned target sequence. Therefore, the single base substitution error rate for both sequence groups combined equals 0.84% for a 165 base stretch, or 0.0051% per base position (0.5 errors per 10,000 bases). This error rate is similar to the one reported by Margulies et al. of 0.004% for individual read substitution errors in test sequences, but much lower than for whole-genome resequencing (0.68%).

A similar analysis of the occurrence of indels in both alignment groups revealed an indel incidence of 3883 (forward primer group) and 3829 (reverse primer group) in a total of 247,052 sequences (is 3.1% in a 165 by stretch). The indel occurrence rate therefore equals 0.01891% per base position (1.89 indels per 10,000 bases). The indel rate is significant higher than the base substitution error rate. Both types of sequencing error combined occur on average at a frequency of 2.39 per 10,000 bases, or 0.024 per base position. This error rate is much lower than reported by Margulies et al., and may be explained by the absence of long homopolymer stretches in the eIF4e exon 1 sequence.

Detection of a Mutation in the Target Locus

Because the objective of this screen is the identification of (EMS)-induced point mutations (preferentially C→T and G→A mutations), all sequences representing indels in comparison to the reference sequence were discarded for the sake of the analysis in this example. Most of the single base substitutions occurred only once in any given 3D pool, some occurred 2 or 3 times, or rarely more often. Since these single base substitutions occur more or less uniformly at every position of the aligned sequence, and at a more or less uniform frequency of 0.005% per base, they were assumed to represent sequencing errors, and not specific mutations that exist in the mutant library. However, at a few specific base positions in the scanned sequence, a much higher incidence of a specific single base sequence difference occurs. Such single base sequence differences reveal mutations in the library, when the following criteria are fulfilled:

1. the single base sequence difference represents an C→T or G→A mutation;
2. the incidence is higher than 20 per 10,000 sequence reads per 3D pool;
3. the single base sequence difference occurs in precisely one and not more than one X-pool, Y-pool and Z-pool.

In this example, one such mutation was found in the alignment group corresponding to the reverse primer, at base position 221 of the eIF4E exon 1 sequence. This mutation, a G→A mutation (corresponding to C→T in the complementary strand) occurred in pool X12 at a frequency of 70 per 10,000 sequences, in pool Y3 at a frequency of 33 per 10,000 and in pool Z6 at 62 per 10,000 sequences. This same mutation at the same position did not occur in any of the other pools, not even at background error rates.

The unique occurrence of this G221A mutation in only the three pools allowed the identification of the original 4-fold pool of DNA, representing four M2 families. DNA of each of these four M2 families was amplified individually with the primers 06F598 and 06F599 that are identical to the forward and reverse primers of Tables 2 and 3, but without the 5' five base sequence tags. The amplified PCR products were subjected to conventional Sanger sequencing. The sequence of the eIF4E gene in one of the four families (coded "24") revealed a dual peak at position 221, corresponding to an overlapping G and A. This is indicative of an M2 family pool, in which half the alleles are wild-type, and the other half carry the G221A point mutation (FIG. 7). The sequences of the other M2 families around base position 221 were according to the reference (wild-type).

The mutation causes an arginine to glutamine substitution. Seeds of this particular M2 family were planted in the greenhouse in order to select for homozygous mutant individuals, that will be used for phenotyping.

In a similar manner, two other point mutations were identified in the 454 sequence reads. An estimation of the mutation density of the M82 tomato mutant library therefore equals 3 mutations per 165 by scanned sequence, or 18 mutations per 1000 bases in 3072 M2 families. This corresponds to mutation densities reported for *Arabidopsis* (Greene et al., *Genetics* 164: 731-740, 2003).

The invention claimed is:

1. A method for identifying the source of an amplicon, comprising:
   (a) providing a plurality of pools of amplicons, each pool comprising amplicons from different sources, wherein the amplicons from at least one of the different sources are present in more than one pool, and wherein the amplicons in each pool are tagged with a unique pool-specific identifier;
   (b) sequencing at least part of the amplicons that comprise the pool-specific identifiers;
   (c) assigning one or more of the amplicons to corresponding pools and/or sources using the pool-specific identifiers.

2. The method according to claim 1, wherein the sequencing is carried out by high-throughput sequencing.

3. The method according to claim 2, wherein the high-throughput sequencing is performed on a solid support.

4. The method according to claim 2, wherein the high-throughput sequencing is based on Sequencing-by-Synthesis.

5. The method according to claim 2, wherein the high-throughput sequencing comprises the steps of:
   annealing the tagged nucleic acid fragments to beads, each bead annealing with a single tagged nucleic acid fragment;
   emulsifying the beads in water-in-oil micro reactors, each water-in-oil micro reactor comprising a single bead;
   performing emulsion PCR to amplify tagged nucleic acid fragments on the surface of beads,
   optionally, selecting and enriching beads comprising amplified tagged nucleic acid fragments;
   loading the beads in wells, each well comprising a single bead; and
   generating a pyrophosphate signal.

6. The method according to claim 2, wherein the high-throughput sequencing comprises the steps of:
   annealing the tagged nucleic acid fragments to a surface comprising first and second primers or first and second primer binding sequences respectively,
   performing bridge amplification to provide clusters of amplified tagged nucleic acid fragments,
   determining the nucleotide sequence of the amplified tagged nucleic acid fragments using labelled reversible terminator nucleotides.

7. The method according to claim 1, wherein the pool-specific identifier is from 4-16 base pairs.

8. The method according to claim 7, wherein the pool-specific identifier is from 4-10 base pairs.

9. The method according to claim 7, wherein the pool-specific identifier is from 4-8 base pairs.

10. The method according to claim 7, wherein the pool-specific identifier is from 4-6 base pairs.

11. The method according to claim 7, wherein the pool-specific identifier does not comprise two or more identical consecutive bases.

12. The method according to claim 7, wherein for two or more pools, the corresponding pool-specific identifiers comprise at least two different nucleotides.

13. The method according to claim 1, wherein the addition of the pool-specific identifier is by ligation of at least one adaptor.

14. The method according to claim 1, wherein the addition of the pool-specific identifier is by amplification with at least one primer.

15. The method according to claim 1, wherein step (c) further comprises clustering/aligning the amplicons that comprise identical nucleic acid sequences in part of the amplicons but different pool-specific identifiers.

16. The method according to claim 1, wherein the amplicons from at least one of the different sources are absent from one or more pools.

* * * * *

SEQUENCE LISTING

```
<160> NUMBER OF SEQ ID NOS: 57

<210> SEQ ID NO 1
<211> LENGTH: 24
<212> TYPE: DNA
<213> ORGANISM: Artificial
<220> FEATURE:
<223> OTHER INFORMATION: Synthetic

<400> SEQUENCE: 1
cacacatggc agcagctgaa atgg                                          24

<210> SEQ ID NO 2
<211> LENGTH: 24
<212> TYPE: DNA
<213> ORGANISM: Artificial
<220> FEATURE:
<223> OTHER INFORMATION: Synthetic

<400> SEQUENCE: 2
cacagatggc agcagctgaa atgg                                          24

<210> SEQ ID NO 3
<211> LENGTH: 24
<212> TYPE: DNA
<213> ORGANISM: Artificial
<220> FEATURE:
<223> OTHER INFORMATION: Synthetic

<400> SEQUENCE: 3
cacgaatggc agcagctgaa atgg                                          24

<210> SEQ ID NO 4
<211> LENGTH: 24
<212> TYPE: DNA
<213> ORGANISM: Artificial
<220> FEATURE:
<223> OTHER INFORMATION: Synthetic

<400> SEQUENCE: 4
cacgtatggc agcagctgaa atgg                                          24

<210> SEQ ID NO 5
<211> LENGTH: 24
<212> TYPE: DNA
<213> ORGANISM: Artificial
<220> FEATURE:
<223> OTHER INFORMATION: Synthetic

<400> SEQUENCE: 5
cactcatggc agcagctgaa atgg                                          24

<210> SEQ ID NO 6
```

```
<211> LENGTH: 24
<212> TYPE: DNA
<213> ORGANISM: Artificial
<220> FEATURE:
<223> OTHER INFORMATION: Synthetic

<400> SEQUENCE: 6
cactgatggc agcagctgaa atgg                                           24

<210> SEQ ID NO 7
<211> LENGTH: 24
<212> TYPE: DNA
<213> ORGANISM: Artificial
<220> FEATURE:
<223> OTHER INFORMATION: Synthetic

<400> SEQUENCE: 7
cagacatggc agcagctgaa atgg                                           24

<210> SEQ ID NO 8
<211> LENGTH: 24
<212> TYPE: DNA
<213> ORGANISM: Artificial
<220> FEATURE:
<223> OTHER INFORMATION: Synthetic

<400> SEQUENCE: 8
cagagatggc agcagctgaa atgg                                           24

<210> SEQ ID NO 9
<211> LENGTH: 24
<212> TYPE: DNA
<213> ORGANISM: Artificial
<220> FEATURE:
<223> OTHER INFORMATION: Synthetic

<400> SEQUENCE: 9
cagcaatggc agcagctgaa atgg                                           24

<210> SEQ ID NO 10
<211> LENGTH: 24
<212> TYPE: DNA
<213> ORGANISM: Artificial
<220> FEATURE:
<223> OTHER INFORMATION: Synthetic

<400> SEQUENCE: 10
cagctatggc agcagctgaa atgg                                           24

<210> SEQ ID NO 11
<211> LENGTH: 24
<212> TYPE: DNA
<213> ORGANISM: Artificial
<220> FEATURE:
<223> OTHER INFORMATION: Synthetic

<400> SEQUENCE: 11
cagtcatggc agcagctgaa atgg                                           24

<210> SEQ ID NO 12
<211> LENGTH: 24
<212> TYPE: DNA
<213> ORGANISM: Artificial
<220> FEATURE:
<223> OTHER INFORMATION: Synthetic

<400> SEQUENCE: 12
```
cagtgatggc agcagctgaa atgg                                          24

<210> SEQ ID NO 13
<211> LENGTH: 24
<212> TYPE: DNA
<213> ORGANISM: Artificial
<220> FEATURE:
<223> OTHER INFORMATION: Synthetic

<400> SEQUENCE: 13
catcgatggc agcagctgaa atgg                                          24

<210> SEQ ID NO 14
<211> LENGTH: 24
<212> TYPE: DNA
<213> ORGANISM: Artificial
<220> FEATURE:
<223> OTHER INFORMATION: Synthetic

<400> SEQUENCE: 14
catgcatggc agcagctgaa atgg                                          24

<210> SEQ ID NO 15
<211> LENGTH: 24
<212> TYPE: DNA
<213> ORGANISM: Artificial
<220> FEATURE:
<223> OTHER INFORMATION: Synthetic

<400> SEQUENCE: 15
ctacgatggc agcagctgaa atgg                                          24

<210> SEQ ID NO 16
<211> LENGTH: 24
<212> TYPE: DNA
<213> ORGANISM: Artificial
<220> FEATURE:
<223> OTHER INFORMATION: Synthetic

<400> SEQUENCE: 16
ctagcatggc agcagctgaa atgg                                          24

<210> SEQ ID NO 17
<211> LENGTH: 24
<212> TYPE: DNA
<213> ORGANISM: Artificial
<220> FEATURE:
<223> OTHER INFORMATION: Synthetic

<400> SEQUENCE: 17
ctcacatggc agcagctgaa atgg                                          24

<210> SEQ ID NO 18
<211> LENGTH: 24
<212> TYPE: DNA
<213> ORGANISM: Artificial
<220> FEATURE:
<223> OTHER INFORMATION: Synthetic

<400> SEQUENCE: 18
ctcagatggc agcagctgaa atgg                                          24

<210> SEQ ID NO 19
<211> LENGTH: 24
<212> TYPE: DNA

<213> ORGANISM: Artificial
<220> FEATURE:
<223> OTHER INFORMATION: Synthetic

<400> SEQUENCE: 19
ctcgaatggc agcagctgaa atgg                                        24

<210> SEQ ID NO 20
<211> LENGTH: 24
<212> TYPE: DNA
<213> ORGANISM: Artificial
<220> FEATURE:
<223> OTHER INFORMATION: Synthetic

<400> SEQUENCE: 20
ctcgtatggc agcagctgaa atgg                                        24

<210> SEQ ID NO 21
<211> LENGTH: 24
<212> TYPE: DNA
<213> ORGANISM: Artificial
<220> FEATURE:
<223> OTHER INFORMATION: Synthetic

<400> SEQUENCE: 21
ctctcatggc agcagctgaa atgg                                        24

<210> SEQ ID NO 22
<211> LENGTH: 24
<212> TYPE: DNA
<213> ORGANISM: Artificial
<220> FEATURE:
<223> OTHER INFORMATION: Synthetic

<400> SEQUENCE: 22
ctctgatggc agcagctgaa atgg                                        24

<210> SEQ ID NO 23
<211> LENGTH: 24
<212> TYPE: DNA
<213> ORGANISM: Artificial
<220> FEATURE:
<223> OTHER INFORMATION: Synthetic

<400> SEQUENCE: 23
ctgacatggc agcagctgaa atgg                                        24

<210> SEQ ID NO 24
<211> LENGTH: 24
<212> TYPE: DNA
<213> ORGANISM: Artificial
<220> FEATURE:
<223> OTHER INFORMATION: Synthetic

<400> SEQUENCE: 24
ctgagatggc agcagctgaa atgg                                        24

<210> SEQ ID NO 25
<211> LENGTH: 24
<212> TYPE: DNA
<213> ORGANISM: Artificial
<220> FEATURE:
<223> OTHER INFORMATION: Synthetic

<400> SEQUENCE: 25
ctgcaatggc agcagctgaa atgg                                        24

<210> SEQ ID NO 26
<211> LENGTH: 24
<212> TYPE: DNA
<213> ORGANISM: Artificial
<220> FEATURE:
<223> OTHER INFORMATION: Synthetic

<400> SEQUENCE: 26
ctgctatggc agcagctgaa atgg                                          24

<210> SEQ ID NO 27
<211> LENGTH: 24
<212> TYPE: DNA
<213> ORGANISM: Artificial
<220> FEATURE:
<223> OTHER INFORMATION: Synthetic

<400> SEQUENCE: 27
ctgtcatggc agcagctgaa atgg                                          24

<210> SEQ ID NO 28
<211> LENGTH: 24
<212> TYPE: DNA
<213> ORGANISM: Artificial
<220> FEATURE:
<223> OTHER INFORMATION: Synthetic

<400> SEQUENCE: 28
ctgtgatggc agcagctgaa atgg                                          24

<210> SEQ ID NO 29
<211> LENGTH: 26
<212> TYPE: DNA
<213> ORGANISM: Artificial
<220> FEATURE:
<223> OTHER INFORMATION: Synthetic

<400> SEQUENCE: 29
cacaccccca aaaatttttca acagtg                                       26

<210> SEQ ID NO 30
<211> LENGTH: 26
<212> TYPE: DNA
<213> ORGANISM: Artificial
<220> FEATURE:
<223> OTHER INFORMATION: Synthetic

<400> SEQUENCE: 30
cacagcccca aaaatttttca acagtg                                       26

<210> SEQ ID NO 31
<211> LENGTH: 26
<212> TYPE: DNA
<213> ORGANISM: Artificial
<220> FEATURE:
<223> OTHER INFORMATION: Synthetic

<400> SEQUENCE: 31
cacgacccca aaaatttttca acagtg                                       26

<210> SEQ ID NO 32
<211> LENGTH: 26
<212> TYPE: DNA
<213> ORGANISM: Artificial
<220> FEATURE:

<223> OTHER INFORMATION: Synthetic

<400> SEQUENCE: 32
cacgtcccca aaatttttca acagtg                                        26

<210> SEQ ID NO 33
<211> LENGTH: 26
<212> TYPE: DNA
<213> ORGANISM: Artificial
<220> FEATURE:
<223> OTHER INFORMATION: Synthetic

<400> SEQUENCE: 33
cactccccca aaatttttca acagtg                                        26

<210> SEQ ID NO 34
<211> LENGTH: 26
<212> TYPE: DNA
<213> ORGANISM: Artificial
<220> FEATURE:
<223> OTHER INFORMATION: Synthetic

<400> SEQUENCE: 34
cactgcccca aaatttttca acagtg                                        26

<210> SEQ ID NO 35
<211> LENGTH: 26
<212> TYPE: DNA
<213> ORGANISM: Artificial
<220> FEATURE:
<223> OTHER INFORMATION: Synthetic

<400> SEQUENCE: 35 cagacccccca aaatttttca acagtg                                       26

<210> SEQ ID NO 36
<211> LENGTH: 26
<212> TYPE: DNA
<213> ORGANISM: Artificial
<220> FEATURE:
<223> OTHER INFORMATION: Synthetic

<400> SEQUENCE: 36
cagagcccca aaatttttca acagtg                                        26

<210> SEQ ID NO 37
<211> LENGTH: 26
<212> TYPE: DNA
<213> ORGANISM: Artificial
<220> FEATURE:
<223> OTHER INFORMATION: Synthetic

<400> SEQUENCE: 37 cagcaccccca aaatttttca acagtg                                       26

<210> SEQ ID NO 38
<211> LENGTH: 26
<212> TYPE: DNA
<213> ORGANISM: Artificial
<220> FEATURE:
<223> OTHER INFORMATION: Synthetic

<400> SEQUENCE: 38
cagctcccca aaatttttca acagtg                                        26

```
<210> SEQ ID NO 39
<211> LENGTH: 26
<212> TYPE: DNA
<213> ORGANISM: Artificial
<220> FEATURE:
<223> OTHER INFORMATION: Synthetic

<400> SEQUENCE: 39
cagtccccca aaatttttca acagtg                                              26

<210> SEQ ID NO 40
<211> LENGTH: 26
<212> TYPE: DNA
<213> ORGANISM: Artificial
<220> FEATURE:
<223> OTHER INFORMATION: Synthetic

<400> SEQUENCE: 40
cagtgcccca aaatttttca acagtg                                              26

<210> SEQ ID NO 41
<211> LENGTH: 26
<212> TYPE: DNA
<213> ORGANISM: Artificial
<220> FEATURE:
<223> OTHER INFORMATION: Synthetic

<400> SEQUENCE: 41
catcgcccca aaatttttca acagtg                                              26

<210> SEQ ID NO 42
<211> LENGTH: 26
<212> TYPE: DNA
<213> ORGANISM: Artificial
<220> FEATURE:
<223> OTHER INFORMATION: Synthetic

<400> SEQUENCE: 42
catgccccca aaatttttca acagtg                                              26

<210> SEQ ID NO 43
<211> LENGTH: 26
<212> TYPE: DNA
<213> ORGANISM: Artificial
<220> FEATURE:
<223> OTHER INFORMATION: Synthetic

<400> SEQUENCE: 43
ctacgcccca aaatttttca acagtg                                              26

<210> SEQ ID NO 44
<211> LENGTH: 26
<212> TYPE: DNA
<213> ORGANISM: Artificial
<220> FEATURE:
<223> OTHER INFORMATION: Synthetic

<400> SEQUENCE: 44
ctagccccca aaatttttca acagtg                                              26

<210> SEQ ID NO 45
<211> LENGTH: 26
<212> TYPE: DNA
<213> ORGANISM: Artificial
<220> FEATURE:
<223> OTHER INFORMATION: Synthetic
```

```
<400> SEQUENCE: 45 ctcacccca aaattttca acagtg                                              26

<210> SEQ ID NO 46
<211> LENGTH: 26
<212> TYPE: DNA
<213> ORGANISM: Artificial
<220> FEATURE:
<223> OTHER INFORMATION: Synthetic

<400> SEQUENCE: 46
ctcagcccca aaattttca acagtg                                             26

<210> SEQ ID NO 47
<211> LENGTH: 26
<212> TYPE: DNA
<213> ORGANISM: Artificial
<220> FEATURE:
<223> OTHER INFORMATION: Synthetic

<400> SEQUENCE: 47
ctcgacccca aaattttca acagtg                                             26

<210> SEQ ID NO 48
<211> LENGTH: 26
<212> TYPE: DNA
<213> ORGANISM: Artificial
<220> FEATURE:
<223> OTHER INFORMATION: Synthetic

<400> SEQUENCE: 48
ctcgtcccca aaattttca acagtg                                             26

<210> SEQ ID NO 49
<211> LENGTH: 26
<212> TYPE: DNA
<213> ORGANISM: Artificial
<220> FEATURE:
<223> OTHER INFORMATION: Synthetic

<400> SEQUENCE: 49
ctctccccca aaattttca acagtg                                             26

<210> SEQ ID NO 50
<211> LENGTH: 26
<212> TYPE: DNA
<213> ORGANISM: Artificial
<220> FEATURE:
<223> OTHER INFORMATION: Synthetic

<400> SEQUENCE: 50
ctctgcccca aaattttca acagtg                                             26

<210> SEQ ID NO 51
<211> LENGTH: 26
<212> TYPE: DNA
<213> ORGANISM: Artificial
<220> FEATURE:
<223> OTHER INFORMATION: Synthetic

<400> SEQUENCE: 51 ctgacccca aaattttca acagtg                                              26

<210> SEQ ID NO 52
<211> LENGTH: 26
```

```
<212> TYPE: DNA
<213> ORGANISM: Artificial
<220> FEATURE:
<223> OTHER INFORMATION: Synthetic

<400> SEQUENCE: 52
ctgagcccca aaatttttca acagtg                                      26

<210> SEQ ID NO 53
<211> LENGTH: 26
<212> TYPE: DNA
<213> ORGANISM: Artificial
<220> FEATURE:
<223> OTHER INFORMATION: Synthetic

<400> SEQUENCE: 53
ctgcacccca aaatttttca acagtg                                      26

<210> SEQ ID NO 54
<211> LENGTH: 26
<212> TYPE: DNA
<213> ORGANISM: Artificial
<220> FEATURE:
<223> OTHER INFORMATION: Synthetic

<400> SEQUENCE: 54
ctgctcccca aaatttttca acagtg                                      26

<210> SEQ ID NO 55
<211> LENGTH: 26
<212> TYPE: DNA
<213> ORGANISM: Artificial
<220> FEATURE:
<223> OTHER INFORMATION: Synthetic

<400> SEQUENCE: 55
ctgtccccca aaatttttca acagtg                                      26

<210> SEQ ID NO 56
<211> LENGTH: 26
<212> TYPE: DNA
<213> ORGANISM: Artificial
<220> FEATURE:
<223> OTHER INFORMATION: Synthetic

<400> SEQUENCE: 56
ctgtgcccca aaatttttca acagtg                                      26

<210> SEQ ID NO 57
<211> LENGTH: 287
<212> TYPE: DNA
<213> ORGANISM: Lycopersicon esculentum

<400> SEQUENCE: 57
atggcagcag ctgaaatgga gagaacgatg tcgtttgatg cagctgagaa gttgaaggcc    60
gccgatggag gaggaggaga ggtagacgat gaacttgaag aaggtgaaat tgttgaagaa   120
tcaaatgata cggcatcgta tttagggaaa gaaatcacag tgaagcatcc attggagcat   180
tcatggactt tttggtttga taaccctacc actaaatctc gacaaactgc ttggggaagc   240
tcacttcgaa atgtctacac tttctccact gttgaaaatt tttgggg               287
```